(12) United States Patent
Bosmans et al.

(10) Patent No.: US 7,635,706 B2
(45) Date of Patent: *Dec. 22, 2009

(54) 5HT$_4$-ANTAGONISTIC 4-(AMINOMETHYL)-PIPERIDINE BENZAMIDES

(75) Inventors: Jean-Paul René Marie André Bosmans, Rijkevorsel (BE); Henricus Jacobus Maria Gijsen, Breda (NE); Laurence Anne Mevellec, Louviers (FR)

(73) Assignee: Janssen Pharmaceutica NV, Beerse (BE)

( * ) Notice: Subject to any disclaimer, the term of this patent is extended or adjusted under 35 U.S.C. 154(b) by 501 days.

This patent is subject to a terminal disclaimer.

(21) Appl. No.: 10/560,485

(22) PCT Filed: Aug. 10, 2004

(86) PCT No.: PCT/EP2004/006278

§ 371 (c)(1),
(2), (4) Date: Dec. 12, 2005

(87) PCT Pub. No.: WO2005/003122

PCT Pub. Date: Jan. 13, 2005

(65) Prior Publication Data

US 2007/0032486 A1   Feb. 8, 2007

(30) Foreign Application Priority Data

Jun. 19, 2003 (WO) .................. PCT/EP03/50237

(51) Int. Cl.
*A61K 31/445* (2006.01)
*C07D 401/12* (2006.01)

(52) U.S. Cl. ...................... 514/320; 546/197
(58) Field of Classification Search .................. 514/320; 546/197

See application file for complete search history.

(56) References Cited

U.S. PATENT DOCUMENTS 4,186,135 A * 1/1980 Thominet et al. ........... 548/526
6,544,997 B1 * 4/2003 Bosmans et al. ....... 514/255.05

FOREIGN PATENT DOCUMENTS

EP          0389037 A     9/1990
WO    WO 93/16072 A      8/1993
WO    WO 00/37461 A      6/2000

OTHER PUBLICATIONS

Nakasato et al. "Preparation and formulation . . ." CA 129:27949 (1998).*
Search report for International Application No. PCT/EP/2004/006278.

* cited by examiner

*Primary Examiner*—Celia Chang
(74) *Attorney, Agent, or Firm*—Woodcock Washburn, LLP

(57) ABSTRACT

The present invention is concerned with novel compounds of formula (I) having 5HT$_4$-antagonistic properties. The invention further relates to methods for preparing such novel compounds, pharmaceutical compositions comprising said novel compounds as well as the use as a medicine of said compounds.

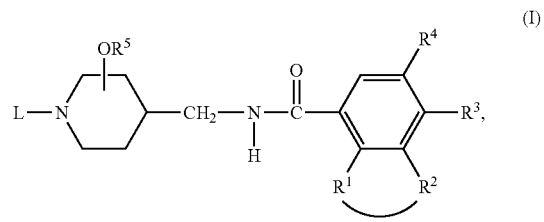

8 Claims, No Drawings

5HT$_4$-ANTAGONISTIC 4-(AMINOMETHYL)-PIPERIDINE BENZAMIDES

CROSS REFERENCE TO RELATED APPLICATIONS

This application is the national stage of Application No. PCT/EP2004/006278, filed Jun. 10, 2004, which application claims priority from Appl. No. PCT/EP03/50237, filed Jun. 19, 2003.

The present invention is concerned with novel compounds of formula (1) having 5HT$_4$-antagonistic properties. The invention further relates to methods for preparing such novel compounds, pharmaceutical compositions comprising said novel compounds as well as the use as a medicine of said compounds.

WO-00/37461 discloses bicyclic benzamides of 3- or 4-substituted 4-(aminomethyl)-piperidine derivatives having 5HT$_4$-antagonistic properties.

The compounds of the present invention differ from the cited art-known compounds structurally, by the presence of a functional group on the 3-position of the benzamide moiety which is other than a hydrogen.

Unexpectedly, the present compounds of formula (I) have improved metabolic stability properties compared with the compounds disclosed in WO-00/37461.

The present invention concerns compounds of formula (I)

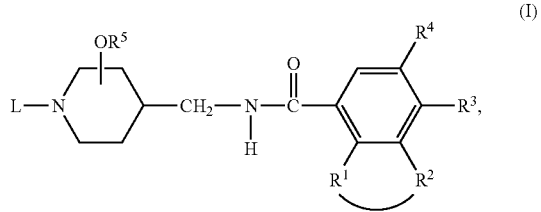

a stereochemically isomeric form thereof, an N-oxide form thereof, or a pharmaceutically acceptable acid or base addition salt thereof, wherein
—R$^1$—R$^2$— is a bivalent radical of formula —O—CH$_2$—O—     (a-1), —O—CH$_2$—CH$_2$—     (a-2), —O—CH$_2$—CH$_2$—O—     (a-3), —O—CH$_2$—CH$_2$—CH$_2$—     (a-4), —O—CH$_2$—CH$_2$—CH$_2$—O—     (a-5), —O—CH$_2$—CH$_2$—CH$_2$—CH$_2$—     (a-6), —O—CH$_2$—CH$_2$—CH$_2$—CH$_2$—O—     (a-7), —O—CH$_2$—CH$_2$—CH$_2$—CH$_2$—CH$_2$—     (a-8), wherein in said bivalent radicals optionally one or two hydrogen atoms on the same or a different carbon atom may be replaced by C$_{1-6}$alkyl or hydroxy,
R$^3$ is C$_{1-6}$alkyl, C$_{1-6}$alkyloxy, or halo;
R$^4$ is hydrogen or halo;
provided that when R$^3$ and R$^4$ are both halo, then the bivalent radical-R$^1$—R$^2$— is of formula (a-5);
R$^5$ is hydrogen or C$_{1-6}$alkyl, and the —OR$^5$ radical is situated at the 3- or 4-position of the piperidine moiety;
L is hydrogen, or L is a radical of formula -Alk-R$^6$     (b-1), -Alk-X—R$^7$     (b-2), -Alk-Y—C(=O)—R$^9$     (b-3), or -Alk-Z-C(=O)—NR$^{11}$R$^{12}$     (b-4), wherein each Alk is C$_{1-12}$alkanediyl; and
R$^6$ is hydrogen; hydroxy; cyano; C$_{3-6}$cycloalkyl; C$_{1-6}$alkylsulfonylamino; aryl or Het;
R$^7$ is C$_{1-6}$alkyl; C$_{1-6}$alkyl substituted with hydroxy; C$_{3-6}$cycloalkyl; aryl or Het;
X is O, S, SO$_2$ or NR$^8$; said R$^8$ being hydrogen or C$_{1-6}$alkyl;
R$^9$ is hydrogen, C$_{1-6}$alkyl, C$_{3-6}$cycloalkyl, hydroxy or aryl;
Y is a direct bond, or NR$^{10}$ wherein R$^{10}$ is hydrogen or C$_{1-6}$alkyl;
Z is a direct bond, O, S, or NR$^{10}$ wherein R$^{10}$ is hydrogen or C$_{1-6}$alkyl;
R$^{11}$ and R$^{12}$ each independently are hydrogen, C$_{1-6}$alkyl, C$_{3-6}$cycloalkyl, or R$^{11}$ and R$^{12}$ combined with the nitrogen atom bearing R$^{11}$ and R$^{12}$ may form a pyrrolidinyl, piperidinyl, piperazinyl or 4-morpholinyl ring both being optionally substituted with C$_{1-6}$alkyl;
aryl represents unsubstituted phenyl or phenyl substituted with 1, 2 or 3 substituents each independently selected from halo, hydroxy, C$_{1-6}$allyl, C$_{1-6}$alkyloxy, C$_{1-6}$alkylcarbonyl, nitro, trifluoromethyl, amino, aminocarbonyl, and aminosulfonyl; and
Het is furanyl; furanyl substituted with C$_{1-6}$alkyl or halo;
    tetrahydrofuranyl; tetrahydrofuranyl substituted with C$_{1-6}$alkyl;
    dioxolanyl; dioxolanyl substituted with C$_{1-6}$alkyl;
    dioxanyl; dioxanyl substituted with C$_{1-6}$alkyl;
    tetrahydropyranyl; tetrahydropyranyl substituted with C$_{1-6}$alkyl;
    2,3-dihydro-2-oxo-1H-imidazolyl; 2,3-dihydro-2-oxo-1H-imidazolyl substituted with one or two substituents each independently selected from halo, or C$_{1-6}$alkyl;
    pyrrolidinyl; pyrrolidinyl substituted with one or two substituents each independently selected from halo, hydroxy, or C$_{1-6}$alkyl;
    pyridinyl; pyridinyl substituted with one or two substituents each independently selected from halo, hydroxy, C$_{1-6}$alkyl;
    pyrimidinyl; pyrimidinyl substituted with one or two substituents each independently selected from halo, hydroxy, or C$_{1-6}$alkyl;
    pyridazinyl; pyridazinyl substituted with one or two substituents each independently selected from hydroxy, C$_{1-6}$alkyloxy, C$_{1-6}$alkyl or halo;
    pyrazinyl; pyrazinyl substituted with one ore two substituents each independently selected from hydroxy, C$_{1-6}$alkyloxy, C$_{1-6}$alkyl or halo.

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; C$_{1-6}$alkyl is meant to include C$_{1-4}$alkyl and the higher homologues thereof having 5 or 6 carbon atoms, such as, for example, 2-methylbutyl, pentyl, hexyl and the like; C$_{3-6}$cycloalkyl is generic to cyclopropyl, cyclobutyl, cyclopentyl and cyclohexyl; $C_{1-12}$alkanediyl defines bivalent straight or branched chain hydrocarbon radicals containing from 1 to 12 carbon atoms such as, for example, methanediyl, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. $C_{1-4}$alkanediyl defines bivalent straight or branched chain hydrocarbon radicals containing from 1 to 4 carbon atoms such as, for example, methanediyl, 1,2-ethanediyl, 1,3-propanediyl, and 1,4-butanediyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

A group of interesting compounds consists of those compounds of formula (I) wherein one or more of the following restrictions apply:
a) —$R^1$—$R^2$— is a radical of formula (a-3); and/or
b) —$R^1$—$R^2$— is a radical of formula (a-5); and/or
c) $R^3$ is $C_{1-6}$alkyl, $C_{1-6}$alkyloxy, or halo; and/or
d) $R^3$ is fluoro; and/or
e) $R^4$ is hydrogen or halo; and/or
f) $R^5$ is hydrogen, or methyl, and the —$OR^5$ radical is situated at the 3- or 4-position of the piperidine ring; and/or
g) $R^5$ is hydrogen, and the —$OR^5$ radical is situated at the 3-position of the piperidine ring; and/or
h) $R^5$ is hydrogen, and the —$OR^5$ radical is situated at the 4-position of the piperidine ring; and/or
i) the —$OR^5$ radical is situated at the 3-position of the piperidine ring and is in the trans position in relation to the methylene on the 4-position of the piperidine moiety; and/or
j) the —$OR^5$ radical is situated at the 3-position of the piperidine ring and is in the trans position in relation to the methylene on the 4-position of the piperidine moiety and the absolute configuration of said piperidine moiety is (3S, 4S); and/or
k) L is hydrogen;
l) L is a radical of formula (b-1), (b-2), (b-3) or (b-4); or
m) L is a radical of formula (b-1) wherein Alk is $C_{1-4}$alkanediyl, and $R^6$ is hydrogen, hydroxy, cyano, $C_{1-6}$alkylsulfonylamino, or Het representing tetrahydrofuranyl, dioxolanyl, or 2,3-dihydro-2-oxo-1H-imidazolyl substituted with $C_{1-6}$alkyl; or L is a radical (b-2) wherein Alk is $C_{1-4}$alkanediyl, and X represents O and $R^7$ is $C_{1-6}$alkyl, $C_{1-6}$alkyl substituted with hydroxy, or aryl representing phenyl substituted with aminosulfonyl; or L is a radical (b-2) wherein Alk is $C_{1-4}$alkanediyl, and X represents $NR^8$ wherein $R^8$ is hydrogen and $R^7$ is $C_{1-6}$alkyl, or Het representing pyrazinyl substituted with $C_{1-6}$alkyl; or L is a radical (b-2) wherein Alk is $C_{1-4}$alkanediyl, and X represents $SO_2$ and $R^7$ is $C_{1-6}$alkyl; or L is a radical (b-3) wherein Alk is $C_{1-4}$alkanediyl, and Y is a direct bond and $R^9$ is hydroxy; or L is a radical of formula (b-4) wherein Alk is $C_{1-4}$alkanediyl, and Z is a direct bond, and $R^{11}$ and $R^{12}$ represent both hydrogen.

Other interesting compounds are those compounds of formula (I) wherein
—$R^1$—$R^2$— is a bivalent radical of formula $$-O-CH_2-CH_2-O- \quad (a\text{-}3),$$

$$-O-CH_2-CH_2-CH_2-O- \quad (a\text{-}5),$$

$R^3$ is $C_{1-6}$alkyl, $C_{1-6}$alkyloxy, or halo;
$R^4$ is hydrogen or halo;
$R^5$ is hydrogen or $C_{1-6}$alkyl, and the —$OR^5$ radical is situated at the 3- or 4-position of the piperidine moiety;
L is hydrogen, or L is a radical of formula $$\text{-Alk-}R^6 \quad (b\text{-}1),$$

$$\text{-Alk-X-}R^7 \quad (b\text{-}2),$$

$$\text{-Alk-Y-C}(\!=\!\!O)\text{-}R^9 \quad (b\text{-}3), \text{ or}$$

$$\text{-Alk-Z-C}(\!=\!\!O)\text{-}NR^{11}R^{12} \quad (b\text{-}4),$$

wherein each Alk is $C_{1-12}$alkanediyl; and
$R^6$ is hydrogen, hydroxy, cyano, $C_{1-6}$alkylsulfonylamino, or Het;
$R^7$ is $C_{1-6}$alkyl; $C_{1-6}$alkyl substituted with hydroxy; aryl or Het;
X is O, $SO_2$ or $NR^8$; said $R^8$ being hydrogen;
$R^9$ is hydroxy;
Y is a direct bond;
Z is a direct bond;
$R^{11}$ and $R^{12}$ each independently are hydrogen;
aryl represents unsubstituted phenyl substituted with aminosulfonyl; and
Het is tetrahydrofuranyl;
  dioxolanyl;
  2,3-dihydro-2-oxo-1H-imidazolyl substituted with $C_{1-6}$alkyl; or
  pyrazinyl substituted with $C_{1-6}$alkyl.

Particular compounds are those compounds of formula (1) wherein the —$OR^5$ radical, preferably representing hydroxy or methoxy, is situated at the 3-position of the piperidine moiety having the trans configuration, i.e. the —$OR^5$ radical is in the trans position in relation to the methylene on the piperidine moiety.

More particular compounds are those compounds of formula (I) wherein the bivalent radical —$R^1$—$R^2$— is a radical of formula (a-3) or (a-5), the —$OR^5$ radical represents hydroxy and is situated at the 3-position of the piperidine moiety having the (3S-trans) configuration which corresponds to absolute (3S, 4S) configuration of said piperidine moiety.

Preferred compounds are those more particular or more particular compounds wherein L is a radical of formula (b-1) wherein Alk is $C_{1-4}$alkanediyl, and $R^6$ is hydrogen, hydroxy, cyano, $C_{1-6}$alkylsulfonylamino, or Het representing tetrahydrofuranyl, dioxolanyl, or 2,3-dihydro-2-oxo-1H-imidazolyl substituted with $C_{1-6}$alkyl.

Other preferred compounds are those particular or more particular compounds wherein L is a radical (b-2) wherein Alk is $C_{1-4}$alkanediyl, and X represents O and $R^7$ is $C_{1-6}$alkyl, $C_{1-6}$alkyl substituted with hydroxy, or aryl representing phenyl substituted with aminosulfonyl.

Yet other preferred compounds are those particular or more particular compounds L is a radical (b-2) wherein Alk is $C_{1-4}$alkanediyl, and X represents $NR^8$ wherein $R^8$ is hydrogen and $R^7$ is $C_{1-6}$alkyl, or Het representing pyrazinyl substituted with $C_{1-6}$alkyl.

Still other preferred compounds are those particular or more particular compounds wherein L is a radical (b-2) wherein Alk is $C_{1-4}$alkanediyl, and X represents $SO_2$ and $R^7$ is $C_{1-6}$alkyl.

More other preferred compounds are those particular or more particular compounds wherein L is a radical (b-3) wherein Alk is $C_{1-4}$alkanediyl, and Y is a direct bond and $R^9$ is hydroxy.

Still more other preferred compounds are those particular or more particular compounds wherein L is a radical of formula (b-4) wherein Alk is $C_{1-4}$alkanediyl, and Z is a direct bond, and $R^{11}$ and $R^{12}$ represent both hydrogen compounds wherein.

Most preferred compounds are those particular or more particular compounds wherein $R^3$ is methoxy and $R^4$ is hydrogen.

The compounds of formula (I) can be prepared by reacting an intermediate of formula (II) with an carboxylic acid derivative of formula (III) or, optionally a reactive functional derivative thereof, such as, e.g. carbonyl imidazole derivatives, acyl halides or mixed anhydrides. Said amide-bond formation may be performed by stirring the reactants in an appropriate solvent, optionally in the presence of a base, such as triethylamine.

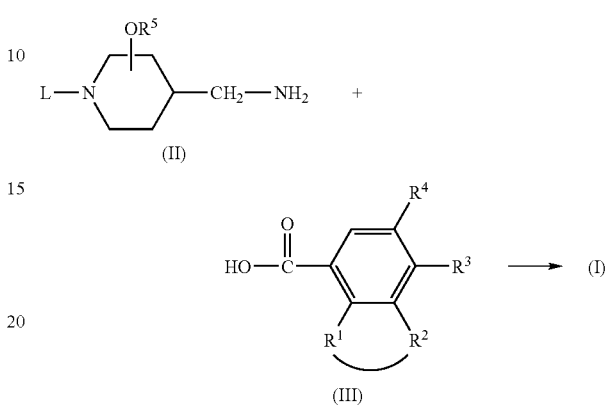

Compounds of formula (I-b), defined as compounds of formula (I) wherein L is other than hydrogen, can generally be prepared by N-alkylating an intermediate of formula (I-a) with an intermediate of formula (IV), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The compounds of formula (I-a) are defined as compounds of formula (I) wherein L represents hydrogen. The reaction can be performed in a reaction-inert solvent such as, for example, acetonitrile, 2-pentanol, isobutanol, dimethyl acetamide or DMF, and optionally in the presence of a suitable base such as, for example, sodium carbonate, potassium carbonate, N-methylpyrrolidone or triethylamine. Stirring may enhance the rate of the reaction. The reaction may conveniently be carried out at a temperature ranging between room temperature and the reflux temperature of the reaction mixture.

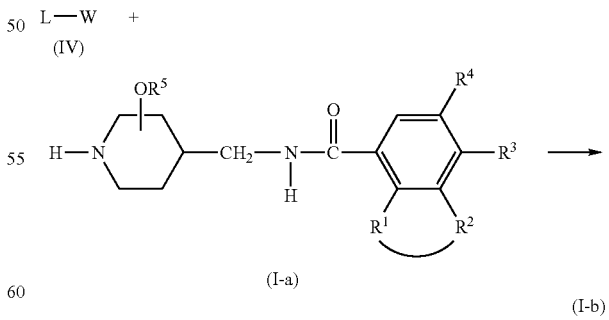

Alternatively, compounds of formula (I-b) can also be prepared by reductively N-alkylating a compound of formula (I-a) with an intermediate of formula L'=O (V), wherein L'=O represents a derivative of formula L-H wherein two geminal hydrogen atoms are replaced by oxygen, following art-known reductive N-alkylation procedures.

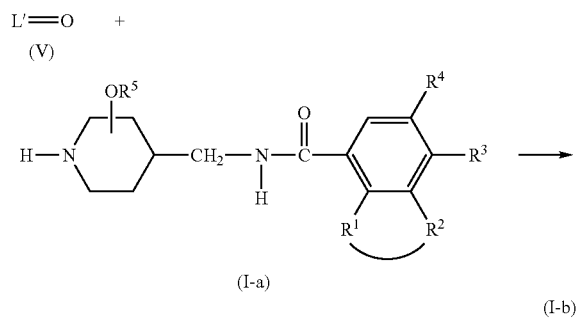

Said reductive N-alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Compounds of formula (I-a) can be prepared by reacting an intermediate of formula (VI), wherein PG represents an appropriate art-known protective group, such as for example a tert-butoxycarbonyl or a benzyl group or a photoremovable group, with an acid of formula (III), or an appropriate reactive functional derivative thereof, such as for example carbonyl imidazole derivatives, and subsequent deprotection of the thus formed intermediate, i.e. removal of PG by art-known methods.

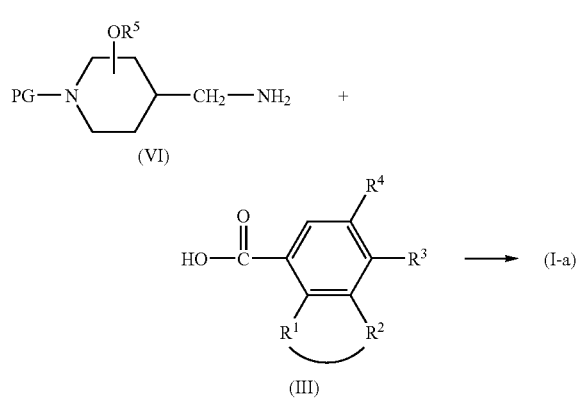

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art. For example, intermediates of formula (II) can be prepared according to the methodologies described in WO-99/02156 or WO-00/37461.

Intermediates of formula (VI) can be prepared according to the general methodology described in WO-99/02156 or WO-00/37461 for the therein described intermediates of formula (VII).

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pro-drugs thereof, the pharmaceutically acceptable salts and stereoisomeric forms thereof possess $5HT_4$-antagonistic properties as described in Example C.1.

Furthermore the compounds of formula (I) have shown improved metabolic stability over the structurally related compounds of WO-00/37461 as described in Example C.2. These advantegous metabolic stability properties result in a reduced risk of drug-drug interaction on the level of cytochrome P450 enzymes such as e.g. CYP1A2, CYP3A4, CYP2D6, CYP2C9 and CYP2C19 and therefore the present compounds have an improved drug safety profile. Furthermore these advantageous metabolic stability properties may allow for a once daily administration of the compounds of formula (I) instead of the usual administration of the active ingredient on a regimen of between two or four intakes per day thereby giving more patient compliance.

In view of the $5HT_4$-antagonistic properties of the compounds of the present invention, the subject compounds may generally be used in the treatment or prophylaxis of gastrointestinal conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

It is also believed that the compounds of formula (I) are useful in the prevention or prophylaxis of a disturbed, hampered or impaired gastric accommodation such as dyspepsia. Dyspeptic symptoms are for example epigastric pressure, a lack of appetite, feeling of fullness, early satiety, nausea, vomiting, bloating and gaseous eructation.

The compounds of formula (I) may also be of use in the treatment of other $5HT_4$-related disorders such as boulimia and hyperphagia.

In view of the utility of the compounds of formula (I), it follows that the present invention also provides a method of treating warm-blooded animals, including humans, (generally called herein patients) suffering from gastrointestinal conditions such as irritable bowel syndrome (IBS). Consequently a method of treatment is provided for relieving patients suffering from conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

The compounds of formula (I) may also be of potential use in other gastrointestinal disorders, such as those associated with upper gut motility. In particular, they are of potential use in the treatment of gastric symptoms of gastro-oesophageal reflux disease, such as heartburn (including episodic heartburn, nocturnal heartburn, and meal-induced heartburn).

Furthermore, the $5HT_4$-antagonistic compounds of formula (I) may also be of potential use in the treatment or prophylaxis of bladder hypersensitivity, overactive bladder, lower urinary tract symptoms, benign prostatic hypertrophy (BPH), prostatis, detrusor hyperreflexia, outlet obstruction, urinary frequency, nocturia, urinary urgency, pelvic hypersensitivity, urge incontinence, urethritis, prostatodynia, cystitis, idiophatic bladder hypersensitivity, urinary incontinence or urinary incontinence associated with irritable bowel syndrome. In this respect, it may be advantageous to combine the $5HT_4$-antagonistic compounds of formula (I) with an alpha-adrenoceptor antagonist such as alfuzosin, indoramin, tamsulosin, doxazosin, terazosin, abanoquil, or prazosin in order to obtain pharmaceutical compositions comprising such an alpha-adrenoceptor antagonist, and a $5$-$HT_4$-receptor antagonist of formula (I).

Hence, the present invention provides compounds of formula (I) for use as a medicine, and in particular the use of compounds of formula (I) for the manufacture of a medicine for treating gastrointestinal conditions such as hypermotility, IBS, constipation- or diarrhea-predominant IBS, pain- and non-pain predominant IBS, bowel hyper-sensitivity, and the reduction of pain associated with gastrointestinal hypersensitivity and/or hyperactivity. Both prophylactic and therapeutic treatment are envisaged.

In view of the $5HT_4$-antagonistic properties of the compounds of the present invention, the subject compounds may also be of use in treating or preventing $5HT_4$-related CNS disorders in a human. In particular, the compounds of formula (I) can be used to treat a variety of CNS disorders including but not limited to drug substance abuse, cognitive disorders such as Alzheimer's disease, senile dementia; behavioral disorders such as schizophrenia, mania, obsessive-compulsive disorder and psychoactive substance use disorders; mood disorders such as depression, bipolar affective disorder, anxiety and panic disorder; disorders of control of autonomic function such as hypertension and sleep disorders; obsessive/compulsive disorders including anorexia and bulimia, and neuropsychiatric disorders, such as Gilles de la Tourette's syndrome, and Huntington's disease.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not-cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro4,1',6'- trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The formulations of the present invention may optionally include an anti-flatulent, such as simethicone, alpha-D-galactosidase and the like.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

In general it is contemplated that a therapeutically effective amount would be from about 0.0001 mg/kg to about 1 mg/kg body weight, preferably from about 0.001 mg/kg to about 0.5 mg/kg body weight.

EXPERIMENTAL PART

In the procedures described hereinafter the following abbreviations were used: "ACN" stands for acetonitrile; "THF", which stands for tetrahydrofuran; "DCM" stands for dichloromethane; "DIPE" stands for diisopropylether; "EtOAc" stands for ethyl acetate; "NE$_4$OAc" stands for ammonium acetate; "HOAc" stands for acetic acid; "MIK" stands for methyl isobutyl ketone.

For some chemicals the chemical formula was used, e.g. NaOH for sodium hydroxide, Na$_2$CO$_3$ for sodium carbonate, K$_2$CO$_3$ for potassium carbonate, H$_2$ for hydrogen gas, N$_2$ for nitrogen gas, CH$_2$Cl$_2$ for dichloromethane, CH$_3$ OH for methanol, NH$_3$ for ammonia, HCl for hydrochloric acid, NaH for sodium hydride, CaCO$_3$ for calcium carbonate, CO for carbon monoxide, and KOH for potassium hydroxide.

A. Preparation of the Intermediates

Example A. 1 a) Preparation of

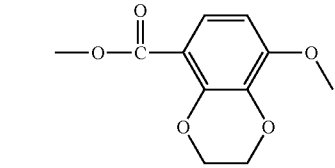

intermediate (1)

A mixture of methyl 2,3-dihydroxy-4-methoxybenzoate (0.176 mol), 1,2-dibromo-ethane (0.282 mol), K$_2$CO$_3$ (0.444 mol) and CuO (1.4 g) in DMF (1000 ml) was stirred for 6 hours, cooled, filtered and the filtrate was evaporated. Water (300 ml) was added. The mixture was extracted twice with DCM (300 ml). The organic layer was separated, washed with a saturated NaHCO$_3$ solution, dried, filtered and the solvent was evaporated. The residue was triturated in DIPE. The precipitate was filtered off and dried, yielding 32.1 g of methyl 2,3-dihydro-8-methoxy-1,4-benzodioxin-5-carboxylate (intermediate 1, mp. 84° C.).

b) Preparation of

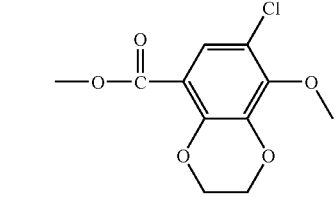

intermediate (2)

A mixture of intermediate (1) (0.118 mol) and N-chlorosuccinimide (0.125 mol) in ACN (350 ml) was stirred at room temperature for two days. The solvent was evaporated and the residue was partitioned between DCM (500 ml) and water (500 ml). The organic layer was separated, dried, filtered and the solvent was evaporated. A part of the residue was crystallized from a mixture of DIPE and ACN, yielding methyl 7-chloro-2,3-dihydro-8-methoxy-1,4-benzodioxin-5-carboxylate (intermediate 2, mp. 99° C.)

c) Preparation of

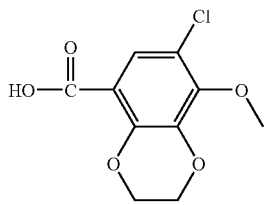

intermediate (3)

A mixture of intermediate (2) (0.138 mol) in a 2N NaOH solution (500 ml) was stirred and refluxed for 1 hour, then cooled and washed with DCM. The mixture was separated into its layers. The aqueous layer was acidified with a concentrated HCl solution until pH=2. The solid was filtered off, washed with water and dried in vacuo. A part (2.5 g) of this fraction was crystallized from methanol. The precipitate was filtered off and dried, yielding 0.88 g of 7-chloro-2,3-dihydro-8-methoxy-1,4-benzodioxin-5-carboxylic acid (intermediate 3, mp. 172° C.).

Example A.2 a) Preparation of

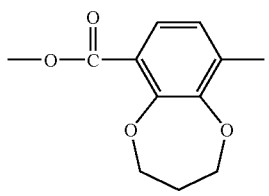

intermediate (4)

A mixture of 2,3-dihydroxy-4-methyl-benzoic acid methylester (1.2 mol), 1,3-dibromo-propane (152 ml) and K$_2$CO$_3$ (380 g) in 2-propanone (2500 ml) was stirred and refluxed for 20 hours. The reaction mixture was cooled, filtered and the filtrate was evaporated, yielding 300 g of intermediate (4).

b) Preparation of

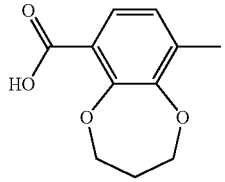

intermediate (5)

A mixture of intermediate (4) (1.12 mol) in NaOH (2 M) (1800 ml) and THF (500 ml) was stirred and refluxed for 3 hours. The reaction mixture was cooled and the organic solvent was evaporated. The aqueous concentrate was acidified with HCl and the resulting precipitate was filtered off, washed with water, and dried, yielding 403 g of intermediate (5).

Example A.3 a) Preparation of

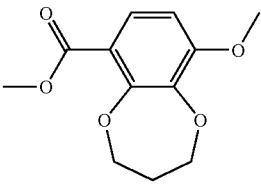

intermediate (6)

A mixture of 2,3-dihydroxy-4-methoxy benzoic acid methyl ester (0.45 mol), 1,3-dibromopropane (0.72 mol), K$_2$CO$_3$ (155 g) and CuO (3.6 g) in DMF (2500 ml) was stirred at 120° C. to 130° C. for 7 hours, cooled and filtered. The solvent was evaporated. HCl (aqueous solution of 0.5 N, 1000 ml)) was added. The mixture was extracted twice with DCM (750 ml). The organic layer was separated, dried, filtered and the solvent was evaporated. The residue was purified by column chromatography over silica gel (eluent:hexane/ethyl acetate/DCM 70/30/15). The pure fractions were collected and the solvent was evaporated. The residue was crystallized from DIPE, yielding methyl 3,4-dihydro-9-methoxy-2H-1,5-benzodioxepin-6-carboxylate (intermediate 6).

b) Preparation of

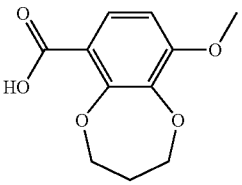

intermediate (7)

A NaOH solution (500 ml, 2N) was added to a solution of intermediate (6) in THF (250 ml). The mixture was stirred at room temperature overnight. The solvent was evaporated partially. The residue was extrated with DCM. The mixture was separated into its layers. The aqueous layer was acidified with a concentrated HCl solution until pH=1 to 2. The solid was filtered off, washed with water and dried, yielding 35.5 g of 9-methoxy-3,4-dihydro-2H-1,5-benzodioxepin-6-carboxylic acid (intermediate 7).

Example A.4 a) Preparation of

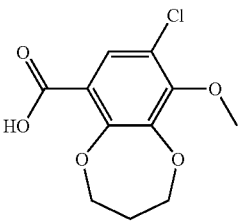

intermediate (8)

Intermediate (7) was converted into 8-chloro-3,4-dihydro-9-methoxy-2H-1,5-benzodioxepin-6-carboxylic acid (intermediate 8, mp. 173° C.) using the same procedure with N-chlorosuccinimide as described in Example A.1.b).

Example A.5 a) Preparation of

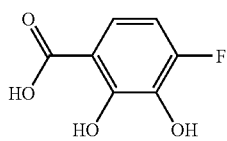

intermediate (9)

A mixture of 3-fluoro-1,2-benzenediol (0.078 mol) and $K_2CO_3$ under $CO_2$ (gas, 50 atm or 5,1 M.Pa) was stirred at 170° C. for 16 hours. The reaction mixture was acidified with an aqueous HCl solution, and the solvent was evaporated. Diethyl ether (500 ml) was added to the residue and the mixture was stirred for 15 minutes, cooled, then filtered over celite. The filtrate's solvent was evaporated, yielding 3.8 g of intermediate (9).

b) Preparation of

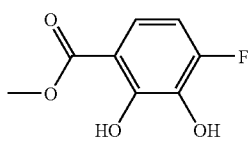

intermediate (10)

Sulfuric acid (20 ml) was added to methanol (60 ml), giving mixture (I). Intermediate (9) (0.022 mol) was dissolved in methanol (70 ml) and added to mixture (I). The reaction mixture was stirred and refluxed for 20 hours. The solvent was evaporated and the residue was partitioned between ethyl acetate/water. The organic layer was dried and the solvent was evaporated. The reaction was repeated several times with crude mixture and all product fractions were combined, yielding 31 g of intermediate (10).

c) Preparation of

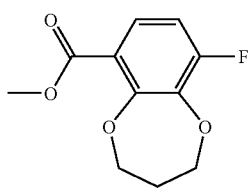

intermediate (11)

A mixture of intermediate (10) (0.166 mol) and $K_2CO_3$ (0.365 mol) in 1,3-dibromo-propane (0.166 mol) and acetone (500 ml) was stirred and refluxed for 24 hours. The reaction mixture was cooled, filtered and the solvent was evaporated. The residue was purified by column chromatography over silica gel. The product fractions were collected and the solvent was evaporated. The residue was purified by high-performance liquid chromatography (reversed phase). The product fractions were collected and the solvent was evaporated, yielding 3 g of intermediate (11).

d) Preparation of

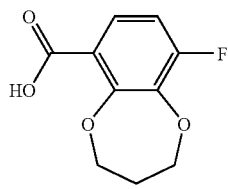

intermediate (12)

A mixture of intermediate (11) (0.013 mol) in NaOH (80 ml, 2N) and THF (50 ml) was stirred at 30° C. for 6 hours. The solvent was partly evaporated and the concentrate was cooled on ice and acidified with HCl (conc.). The solids were filtered off, washed with water and dried, yielding 2.45 g of intermediate (12).

Example A.6 a) Preparation of

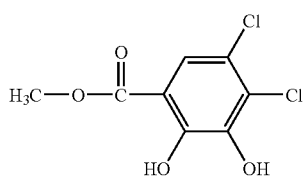

intermediate (13)

A mixture of 5-chloro-2,3-dihydroxy benzoic acid methyl ester (0.49 mol), in acetic acid (2000 ml) was stirred and refluxed. A solution of N-chlorosuccinimide (0.49 mol) in acetic acid (600 ml) was added dropwise at reflux. The reaction mixture was stirred and refluxed for 30 minutes. Extra solution of N-chlorosuccinimide (0.075 mol) in acetic acid (100 ml) was added dropwise at reflux. The reaction mixture was stirred and refluxed for 30 minutes, then cooled and poured out into water (500 ml). The residue was extracted with toluene (3 times). The separated organic layer was washed with water, dried, and evaporated. The residue was crystallized from DIPE and petroleumether, yielding 70 g of intermediate (13).

b) Preparation of

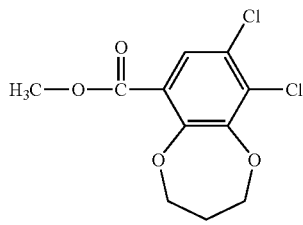

intermediate (14)

A mixture of intermediate (13) (0.3 mol), 1,3-dibromopropane (0.35 mol) and $K_2CO_3$ (0.7 mol) in 2-propanone (1000 ml) was stirred and refluxed for 30 hours. The reaction mixture was cooled, diluted with water (2000 ml) and extracted twice with DCM. The separated organic layer was washed with water, dried, and the solvent was evaporated. The residue was crystallized from DIPE and petroleumbenzine, yielding 55 g of intermediate (14).

c) Preparation of

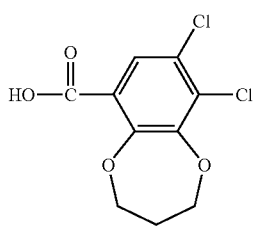

intermediate (15)

A mixture of intermediate (14) (0.2 mol) and KOH (1 mol) in water (1000 ml) was stirred and refluxed for 90 minutes. The reaction mixture was cooled, acidified with HCl and the resulting precipitate was filtered off, washed with water, and dried, yielding 46 g of intermediate (15).

Example A.7 a) Preparation of

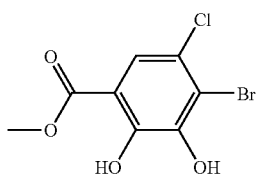

intermediate (16)

A mixture of 5-chloro-2,3-dihydroxy benzoic acid methyl ester (0.1 mol) in acetic acid (250 ml) and N-bromosuccinimide (0.11 mol) was stirred and refluxed for 4 hours. The reaction mixture was cooled and poured out into water (500 ml). The precipitate was filtered and dried, yielding 23 g of intermediate (16).

b) Preparation of

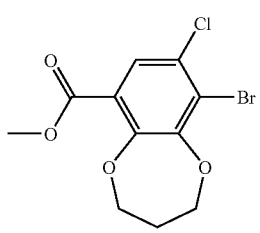

intermediate (17)

A mixture of intermediate (16) (0.7 mol), 1,3-dibromopropane (0.94 mol) and $K_2CO_3$ (1.55 mol) in 2-propanone (1300 ml) was stirred and refluxed for 20 hours. The reaction mixture was cooled, filtered and the solvent was evaporated. The residue was solidified in petroleumether, filtered and dried, yielding 240 g of intermediate (17).

c) Preparation of

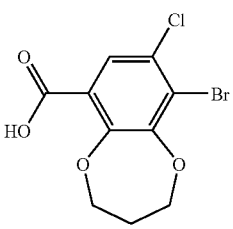

intermediate (18)

A mixture of intermediate (17) (0.053 mol) and KOH (0.2 mol) in water (160 ml) was stirred and refluxed for 90 minutes. The reaction mixture was cooled and the aqueous layer was extracted with DCM. The aqueous layer was acidified with HCl and the resulting precipitate was filtered off, washed with water, and dried, yielding 13 g of intermediate (18).

Example A.8

Preparation of

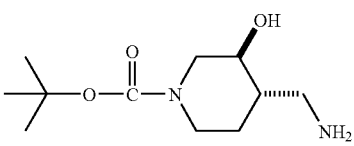

intermediate (19)

A mixture of 1,1-dimethylethyl (trans)-3-hydroxy-4-[[(phenylmethyl)amino]methyl]-1-piperidinecarboxylate [described in WO-00/37461 as intermediate (1-d)] (0.023 mol) in methanol (100 ml) was hydrogenated with palladium-on-carbon (10%, 1 g) as a catalyst. After uptake of hydrogen (1 equivalent), the catalyst was filtered off and the filtrate was evaporated. The residue was solidified in DIPE+ACN, filtered off and dried, yielding 4 g of 1,1-dimethylethyl (trans) 4-(aminomethyl)-3-hydroxy-1-piperidinecarboxylate (intermediate 19, mp. 178° C.).

In an analogous way, but starting from cis-3-hydroxy4-piperidinemethanol (described in *J. Org. Chem.*, 34, pp. 3674-3676 (1969)), 1,1-dimethylethyl (cis)-4-(aminomethyl)-3-hydroxy-1-piperidinecarboxylate (intermediate 20) was prepared.

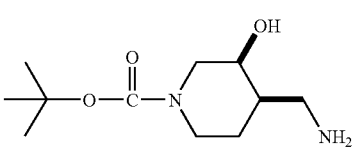

intermediate (20)

Example A.9 a) Preparation of

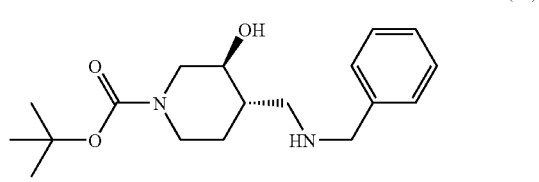

intermediate (21)

1,1-Dimethylethyl (trans)-3-hydroxy-4-[[(phenylmethyl)amino]methyl]-1-piperidinecarboxylate [described in WO-00/37461 as intermediate (1-d)] (2.73 mol) was separated and purified by chiral column chromatography over Chiralcel AD (eluent:hexane/ethanol 80/20). The desired fractions were collected and the solvent was evaporated. Toluene was added and azeotroped on the rotary evaporator, yielding 377 g of 1,1-dimethylethyl (3S-trans)-3-hydroxy-4-[[(phenylmethyl)amino]methyl]-1-piperidinecarboxylate (intermediate 21).

b) Preparation of

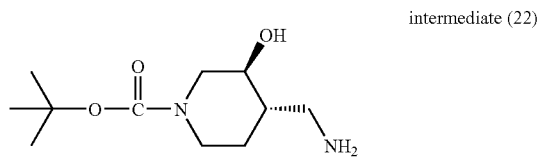

intermediate (22)

A mixture of intermediate (21) (0.028 mol) in methanol (100 ml) was hydrogenated with palladium-on-carbon (10%, 2 g) as a catalyst. After uptake of hydrogen (1 equivalent) the catalyst was filtered off and the filtrate was evaporated, yielding 4.7 g of 1,1-dimethylethyl (3S-trans)-4-(aminomethyl)-3-hydroxy-1-piperidinecarboxylate (intermediate (22); $[\alpha]^{20,D}$=+4.37° (c=24.03 mg/5 ml in $CH_3OH$)).

Example A. 10 a) Preparation of

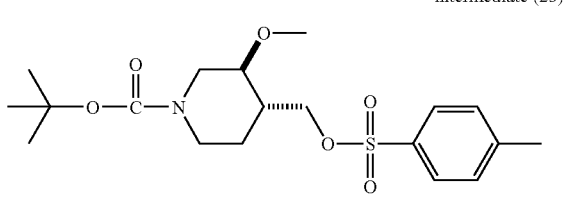

intermediate (23)

Reaction under nitrogen atmosphere. Sodiumhydride (0.3 mol) was added to a solution of 1,1-dimethylethyl trans-3-hydroxy-4-[[[(4-methylphenyl)sulfonyl]oxy]methyl]-1-piperidinecarboxylate [described in WO-00/37461 as intermediate (1-c)] (0.27 mol) in THF (1300 ml). The mixture was stirred for 30 minutes. Methyliodide (0.54 mol) was added and the resulting reaction mixture was stirred for 90 minutes. A small amount of water was added. The solvent was evaporated and the residue was partitioned between water and DCM. The organic layer was separated, dried, filtered and the solvent was evaporated, yielding 1,1-dimethylethyl trans-4-[[[(4-methylphenyl)sulfonyl]oxy]-methyl]-3-methoxy-1-piperidinecarboxylate (intermediate 23).

b) Preparation of

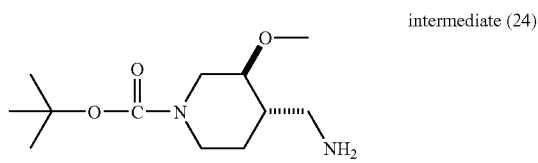

intermediate (24)

A mixture of intermediate (23) (0.065 mol) in THF (250 ml) was treated with liquid $NH_3$ in an autoclave at 125° C. during 16 hours. The reaction mixture was filtered and the filtrate was evaporated. The residue was partitioned between a 5% aqueous NaOH solution and DCM. The organic layer was separated, dried, filtered and the solvent was evaporated, yielding 16 g of 1,1-dimethylethyl (trans)-4-(aminomethyl)-3-methoxy-1-piperidinecarboxylate (intermediate (24).

Example A.11 a) Preparation of

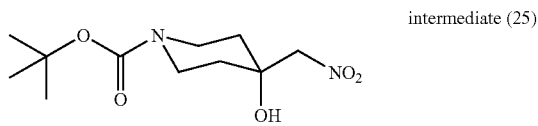

intermediate (25)

A mixture of tert-butyl 4-oxo-1-piperidinecarboxylate (0.1 mol) and nitro-methane (0.1 mol) in methanol (200 ml) was stirred at 10° C. Sodium methanolate (0.11 mol) was added dropwise at 10° C. The reaction mixture was stirred for 20 hours at room temperature. The solvent was evaporated. The residue was taken up into water, then neutralized with acetic acid, then extracted twice with DCM. The separated organic layer was washed with water, dried, filtered and the solvent evaporated. The residue was suspended in DIPE, filtered off, washed and dried, yielding 17.2 g of intermediate (25) (mp. 160° C.).

b) Preparation of

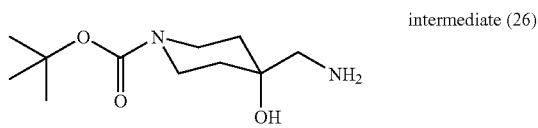

intermediate (26)

A mixture of intermediate (25) (0.058 mol) and acetic acid (12 ml) in methanol (250 ml) was hydrogenated at 14° C. with palladium-on-carbon (10%, 1 g) as a catalyst. After uptake of hydrogen (3 equivalents), the catalyst was filtered off and the filtrate was evaporated. The residue was taken up into ice/water, then alkalized with potassium hydroxide and salted out with $K_2CO_3$. This mixture was extracted twice with DCM. The separated organic layer was dried, filtered and the solvent evaporated. The residue was suspended in DIPE, filtered off, washed and dried, yielding 7.5 g of intermediate (26).

Example A.12 a) Preparation of

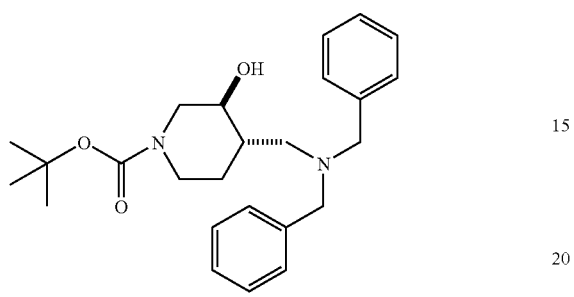

intermediate (27)

A mixture of 1,1-dimethylethyl (trans)-3-hydroxy-4-[[(phenylmethyl)amino]methyl]-1-piperidinecarboxylate (intermediate (1-d) in WO-99/02156) (0.426 mol), benzaldehyde (0.5 mol) and palladium-on-carbon (10%) (5 g) in a thiophene solution (5 ml) and methanol (1000 ml) was stirred at 70-80° C. overnight. The solvent was evaporated. The residue was partitioned between DCM (150 ml) and 5% aqueous NaOH (150 ml). The mixture was separated into its layers. The aqueous layer was extracted with DCM. The combined organic layer was dried, filtered and the solvent was evaporated. The residue was purified by column chromatography over silica gel (eluent: $CH_2Cl_2/(CH_3OH/NH_3)$ 90/10). The pure fractions were collected and the solvent was evaporated. The residue was crystallized from DIPE and a drop of ACN. The precipitate was filtered off and dried, yielding 2.35 g 1,1-dimethylethyl (trans)-4-[[bis(phenylmethyl)amino]methyl]-3-hydroxy-1-piperidinecarboxylate (intermediate 27), mp. 133° C.).

b) Preparation of

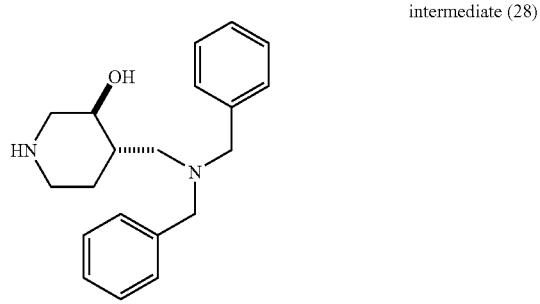

intermediate (28)

A mixture of intermediate (27) (0.284 mol) in 2-propanol (1000 ml) and a mixture of 6N HCL in 2-propanol (250 ml) was stirred and refluxed for 15 minutes and then cooled. The solvent was evaporated. A 5% aqueous NaOH solution (750 ml) was added. The mixture was extracted three times with DCM. The organic layer was separated, dried, filtered and the solvent was evaporated, yielding 88.95 g of (trans)-4-[[bis (phenylmethyl)amino]methyl]-3-piperidinol (intermediate 28).

c) Preparation of

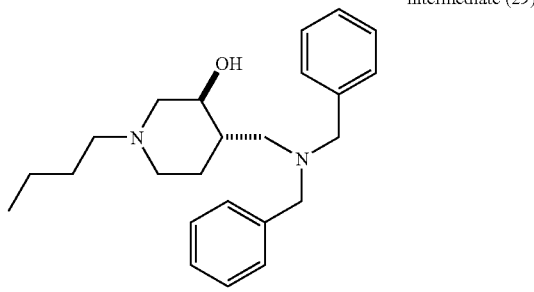

intermediate (29)

A mixture of intermediate (28) (0.083 mol) and butylaldehyde (7 g) in methanol (300 ml) was hydrogenated with palladium-on-carbon (10%) (2 g) as a catalyst in the presence of a thiophene solution (3 ml). After uptake of hydrogen (1 equivalent), the catalyst was filtered over celite and the filtrate was evaporated. The residue was dissolved in aqueous HCl 2N (500 ml). The mixture was washed with toluene and then separated into its layers. The aqueous layer was basified with 50% aqueous NaOH and then extracted three times with toluene. The combined organic layer was dried, filtered and the solvent was evaporated, yielding 29 g of (trans)-4-[[bis (phenylmethyl)amino]-methyl]-1-butyl-3-piperidinol (intermediate 29).

d) Preparation of

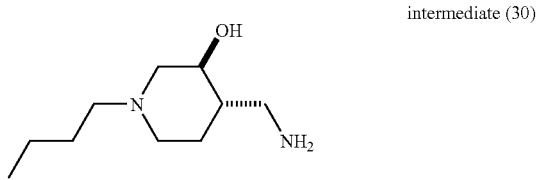

intermediate (30)

A mixture of intermediate (29) (0.079 mol) in methanol (250 ml) was hydrogenated with palladium-on-carbon (10%) (2 g) as a catalyst. After uptake of hydrogen (2 equivalents), the catalyst was filtered over celite and the filtrate was evaporated, yielding 13.8 g of (trans)-4-(aminomethyl)-1-butyl-3-piperidinol (intermediate 30).

Example A.13 a) Preparation of

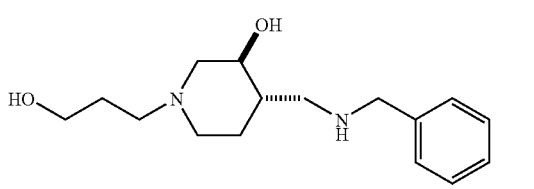

intermediate (31)

A mixture of (trans)-4-[[(phenylmethyl)amino]methyl]-3-piperidinol (prepared as intermediate (6) in WO-00/37461) (0.04 mol), 3-bromo-1-propanol (0.04 mol) and $Na_2CO_3$ (0.08 mol) in methylisobutyl ketone (400 ml) was stirred and refluxed for 18 hours. The solvent was evaporated. The residue was partitioned between water and DCM. The organic layer was separated, dried, filtered and the solvent was evaporated. The residue was purified by column chromatography over silica gel (eluent: CH$_2$Cl$_2$/(CH$_3$OH/NH$_3$) 93/7). The desired fractions were collected and the solvent was evaporated. Toluene was added, then evaporated again, yielding 7.2 g of intermediate (31).

b) Preparation of

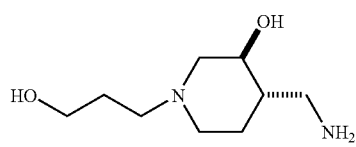

intermediate (32)

A mixture of intermediate (31) (0.026 mol) in methanol (150 ml) was hydrogenated with palladium-on-carbon (10%, 2 g) as a catalyst. After uptake of hydrogen (1 equivalent), the catalyst was filtered off and the filtrate was evaporated, yielding 4.4 g of intermediate (32).

Example A.14 a) Preparation of HO

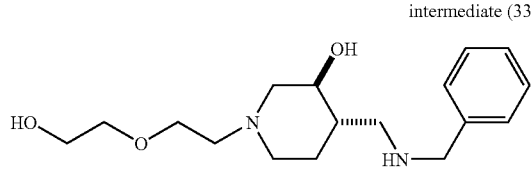

intermediate (33)

A mixture of (trans)-4-[[(phenylmethyl)amino]methyl]-3-piperidinol (prepared as intermediate (6) in WO-00/37461) (0.05 mol), 2-(2-chloroethoxy)-ethanol (0.05 mol) and sodium carbonate (0.1 mol) in MIK (500 ml) was stirred and refluxed for 20 hours. More 2-(2-chloroethoxy)-ethanol (0.02 mol) was added and the reaction mixture was stirred and refluxed for 20 hours. The solvent was evaporated. The residue was partitioned between water and DCM. The organic layer was separated, dried, filtered and the solvent was evaporated. The residue was purified by column chromatography over silica gel (eluent: CH$_2$Cl$_2$/(CH$_3$OH/NH$_3$) 93/). The pure fractions were collected and the solvent was evaporated. Toluene was added and azeotroped on the rotary evaporator, yielding 8.4 g of intermediate (33).

b) Preparation of

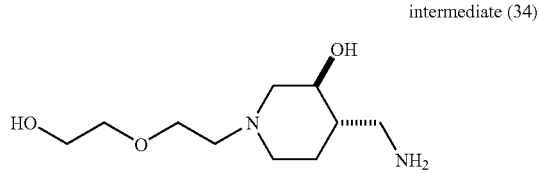

intermediate (34)

A mixture of intermediate (33) (0.027 mol) in methanol (150 ml) was hydrogenated with palladium-on-carbon (10%, 2 g) as a catalyst. After uptake of hydrogen (1 equivalent), the catalyst was filtered off and the filtrate was evaporated, yielding 5.4 g of intermediate (34).

Example A.15 a) Preparation of

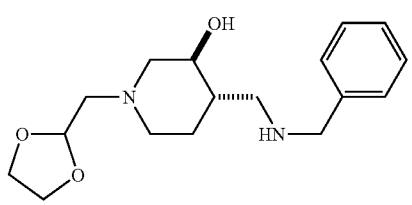

intermediate (35)

A mixture of (trans)-4-[[(phenylmethyl)amino]methyl]-3-piperidinol (prepared as intermediate (6) in WO-00/37461) (0.068 mol), 2-(bromomethyl)-1,3-dioxolane (0.07 mol) and sodium carbonate (0.28 mol) in MIK (500 ml) was stirred and refluxed for 24 hours. The reaction mixture was cooled. The solvent was evaporated. The residue was taken up into DCM, washed with water, dried, filtered and the solvent was evaporated. The residue was purified by column chromatography over silica gel (eluent: CH$_2$Cl$_2$/(CH$_3$OH/NH$_3$) 95/5). The pure fractions were collected and the solvent was evaporated, yielding 10.8 g of intermediate (35).

b) Preparation of

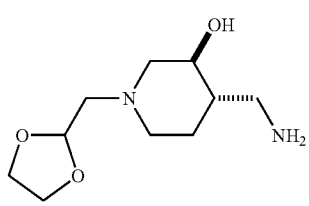

intermediate (36)

A mixture of intermediate (35) (0.035 mol) in methanol (250 ml) was hydrogenated with palladium-on-carbon (10%, 2 g) as a catalyst. After uptake of hydrogen (1 equivalent), the catalyst was filtered off and the filtrate was evaporated, yielding 7.2 g of intermediate (36).

Example A.16 a) Preparation of

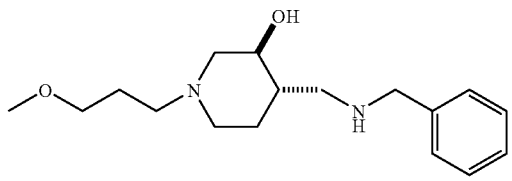

intermediate (37)

A mixture of (trans)-4-[[(phenylmethyl)amino]methyl]-3-piperidinol (prepared as intermediate (6) in WO-00/37461) (0.04 mol), 1-chloro-3-methoxypropane (0.04 mol) and Na$_2$CO$_3$ (0.08 mol) in methylisobutyl ketone (300 ml) was stirred and refluxed for 20 hours, then cooled and the solvent was evaporated. The residue was taken up into DCM, then washed with water, dried, filtered and the solvent was evaporated. The residue was purified by column chromatography over silica gel (eluent: CH$_2$Cl$_2$/(CH$_3$OH/NH$_3$) 97/3). The pure fractions were collected and the solvent was evaporated, yielding 5 g of intermediate (37)

b) Preparation of

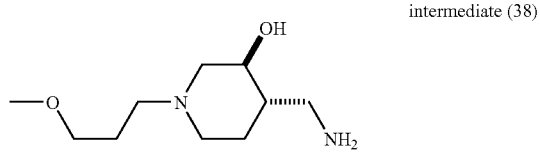

intermediate (38)

A mixture of intermediate (37) (0.016 mol) in methanol (150 ml) was hydrogenated with palladium-on-carbon (10%, 1 g) as a catalyst. After uptake of hydrogen (1 equivalent), the catalyst was filtered off and the filtrate was evaporated, yielding 3.3 g of intermediate (38).

Example A.17 a) Preparation of

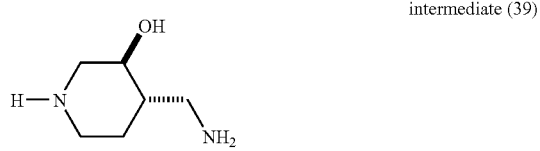

intermediate (39)

1,1-Dimethylethyl (trans)-4-(aminomethyl)-3-hydroxy-1-piperidinecarboxylate (prepared as intermediate (1-e) in WO-00/37461) (0.06 mol) in 2-propanol saturated with HCl (60 ml) and 2-propanol (400 ml) was stirred and refluxed for 30 minutes, then cooled. The solvent was evaporated and co-evaporated with toluene. The residue was dried, yielding 12 g of intermediate (39).

b) Preparation of

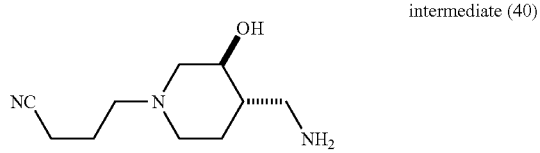

intermediate (40)

A mixture of 4-bromo-butanenitrile (0.06 mol), intermediate (39) (0.06 mol) and Na$_2$CO$_3$ (0.24 mol) in ACN (600 ml) was stirred and refluxed for 20 hours; then cooled and filtered. The solvent was evaporated. The residue was purified by column chromatography over silica gel (eluent: CH$_2$Cl$_2$/(CH$_3$OH/NH$_3$) 85/15). The desired fractions were collected and the solvent was evaporated, yielding 4.5 g of intermediate (40).

Example A.18 a) Preparation of

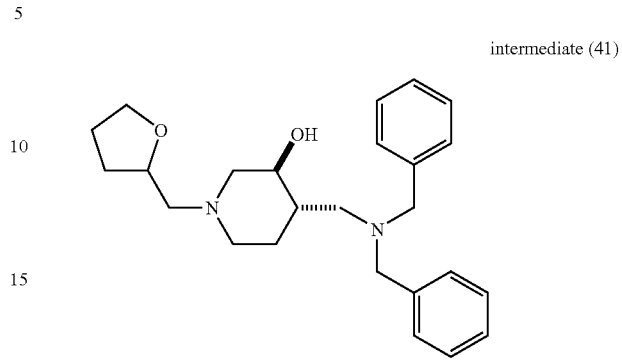

intermediate (41)

Intermediate (28) (0.0387 mol) dissolved in 2-methyl-propanol (200 ml). Tetrahydrofurfuryl methanesulfonate (0.05 mol) and Na$_2$CO$_3$ (0.0774 mol) were added. The reaction mixture was stirred and refluxed for 24 hours; then cooled. The precipitate was filtered off. The solvent was evaporated. The residue was purified by column chromatography over silica gel (eluent: CH$_2$Cl$_2$/CH$_3$OH 97/3). The desired fractions were collected and the solvent was evaporated, yielding 11.1 g of intermediate (41).

b) Preparation of

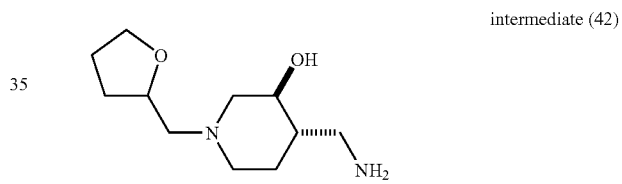

intermediate (42)

Intermediate (41) (0.0279 mol) in methanol (150 ml) was hydrogenated with palladium-on-carbon (10%, 2 g) as a catalyst. After uptake of hydrogen (2 equivalents), the catalyst was filtered off over dicalite and the solvent was evaporated, yielding 5.74 g of intermediate (42).

Example A.19 a) Preparation of

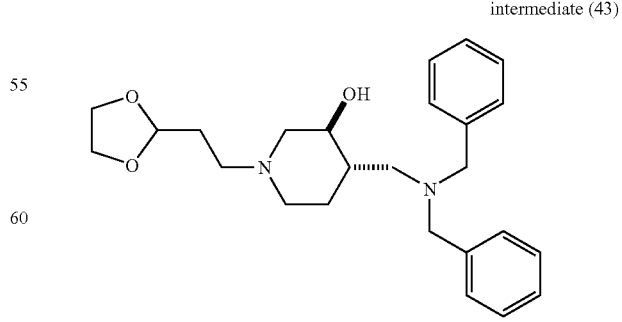

intermediate (43)

A mixture of 2-(2-bromoethyl)-1,3-dioxolane (0.04 mol), intermediate (6) (0.04 mol) and Na$_2$CO$_3$ (10%, 0.08 mol) in MIK (400 ml) was stirred and refluxed for 20 hours and then cooled. The solvent was evaporated. The residue was taken up in DCM and water. The organic layer was separated, dried, filtered and the solvent was evaporated. The residue was purified by column chromatography over silica gel (eluent: $CH_2Cl_2/(CH_3OH/NH_3)$ 96/4). The pure fractions were collected and the solvent was evaporated. Toluene was added and evaporated again, yielding 6g of (trans)-1-[2-(1,3-dioxolan-2-yl)ethyl]-4-[[(phenylmethyl)amino]methyl]-3-piperidinol (intermediate 43).

b) Preparation of

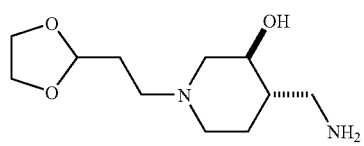

intermediate (44)

A mixture of intermediate (43) (0.019 mol) in methanol (150 ml) was hydrogenated with palladium-on-carbon (10%, 2g) as a catalyst. After uptake of 1 equivalent hydrogen, the catalyst was filtered off and the filtrate was evaporated, yielding 4 g of (trans)-4-(aminomethyl)-1-[2-(1,3-dioxolan-2-yl)ethyl]-3-piperidinol (intermediate 44).

Example A.20

Preparation of

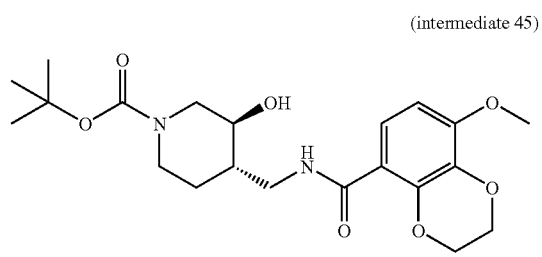

(intermediate 45)

A mixture of 2,3-dihydro-8-methoxy-1,4-benzodioxin-5-carboxylic acid (0.05 mol), 1,1'-carbonyldiimidazole (0.052 mol) in DCM (150 ml) was stirred at room temperature for 30 minutes, giving mixture (I). Said mixture (I) was added to a mixture of 1,1-dimethylethyl (3S-trans)-4-(aminomethyl)-3-hydroxy-1-piperidine carboxylate alpha-hydroxybenzeneacetate (1:1) (0.052 mol) in DCM (100 ml) at room temperature. The mixture was stirred for 48 hours and washed with water. The organic layer was dried, filtered and the solvent was evaporated, yielding 22 g of intermediate (45).

TABLE I-1 intermediates (46) to (60) were prepared according to the same procedure of Example A.20

| Intm. | Structure | Physical data |
|---|---|---|
| 46 | 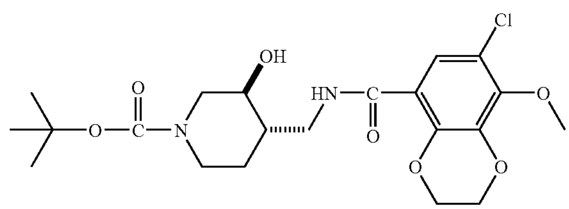 | trans; mp. 145° C. |
| 47 | 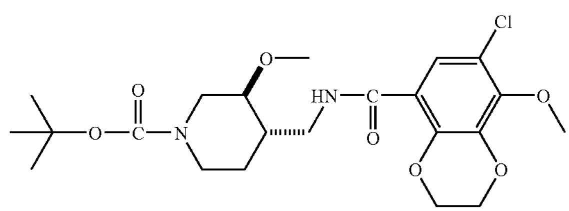 | trans; |
| 48 | 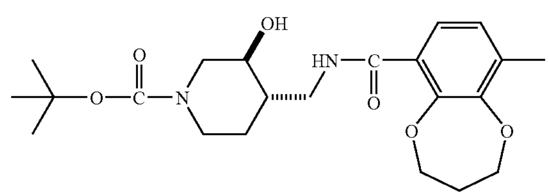 | trans; |

TABLE I-1-continued intermediates (46) to (60) were prepared according to the same procedure of Example A.20

| Intm. | Structure | Physical data |
|---|---|---|
| 49 | 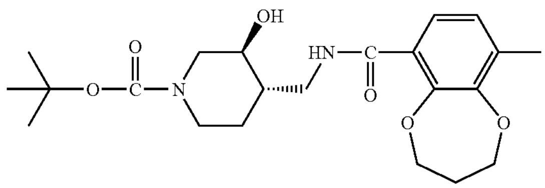 | 3S-trans; |
| 50 | 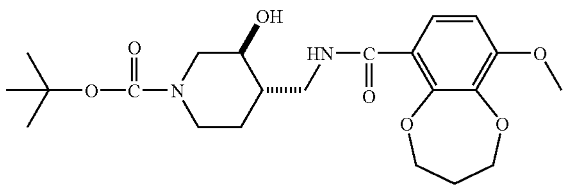 | trans; mp. 165° C. |
| 51 | 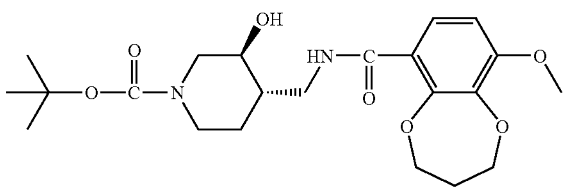 | 3S-trans |
| 52 | 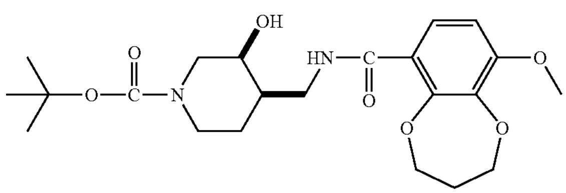 | cis; |
| 53 | 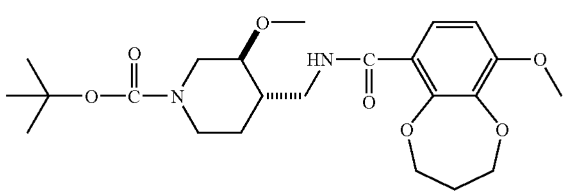 | trans; |
| 54 | 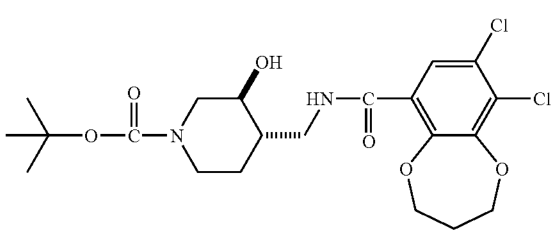 | trans; |
| 55 | 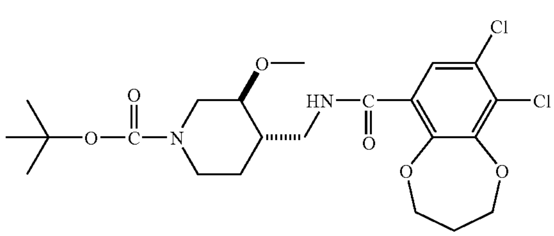 | trans; |

TABLE I-1-continued intermediates (46) to (60) were prepared according to the same procedure of Example A.20

| Intm. | Structure | Physical data |
|---|---|---|
| 56 | 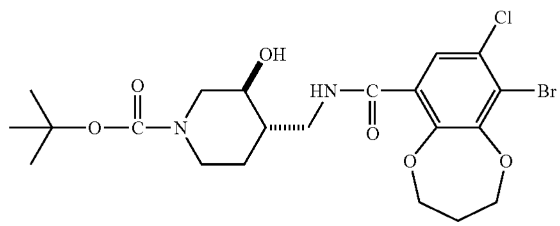 | trans; |
| 57 | 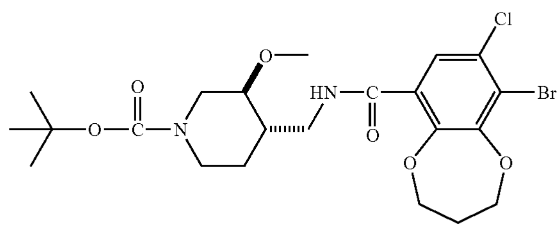 | trans; |
| 58 | 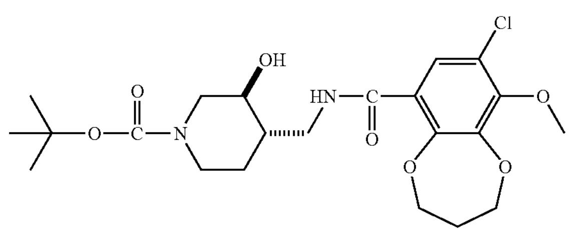 | trans; mp. 157° C. |
| 59 | 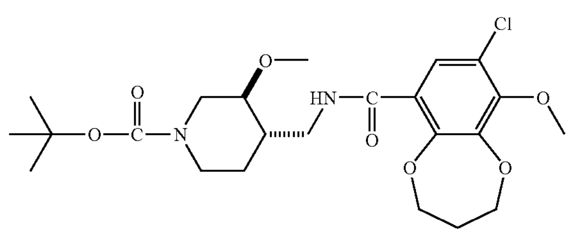 | trans; |
| 60 | 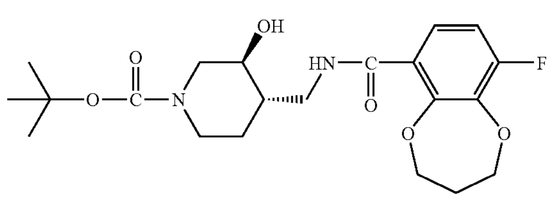 | 3S-trans; |
| 61 | 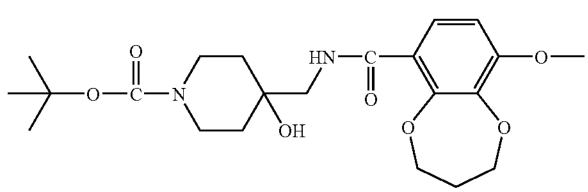 | |

Example A.21 a) Preparation of

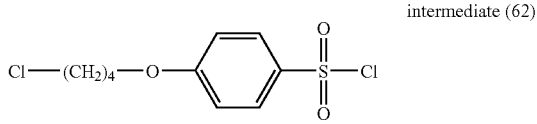

intermediate (62)

A mixture of 4-phenoxybutyl chloride (0.135 mol) in DCM (50 ml) was stirred and cooled to 0° C. Chlorosulfuric acid (0.149 mol) was added dropwise in 45 minutes. The ice bath was removed and the reaction mixture was stirred at room temperature for 2 hours. Then, ethanedioyl dichloride (0.176 mol) was added dropwise, followed by DMF (2 ml). The reaction mixture was stirred at room temperature for 20 hours. Then, the mixture was poured out on ice, extracted with DCM, dried and the solvent was evaporated, yielding intermediate (62).

b) Preparation of

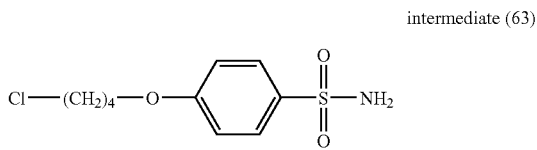

intermediate (63)

A solution of intermediate (62) (0.135 mol) in THF (500 ml) was stirred and cooled to 0° C. then, ammonia (gas) was bubbled through the solution. The reaction mixture was filtered and the solvent was evaporated. DCM (600 ml) was added to the residue and the mixture was washed with HCl (600 ml, 1N). The aqueous layer was separated and extracted with DCM (2 times 300 ml). The combined organic layers were washed with brine, dried and the solvent was evaporated. The residue was crystallised from CH$_3$OH/DIPE, filtered off and dried, yielding 18.5 g of intermediate (63).

In an analogous way, but starting from 4-phenoxypropyl chloride or 4-phenoxyethyl chloride, intermediates (64) and (65) were prepared.

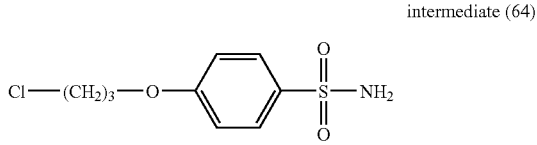

intermediate (64)

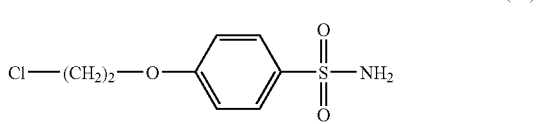

intermediate (65)

Example A.22

Preparation of

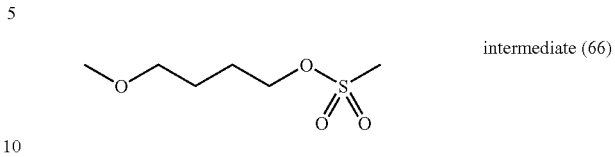

intermediate (66)

4-Methoxy-1-butanol (0.9 mol) was stirred in DCM (1500 ml) and triethylamine (1.35 mol) was added, then methylsulfonyl chloride (1.1 mol) was added dropwise (temperature rise up to 40° C.) and the reaction mixture was stirred for 2 hours at room temperature. The mixture was washed with water. The organic layer was separated, dried and the solvent was evaporated, then co-evaporated with toluene, yielding 167 g of intermediate (66).

For the preparation of the final compounds, also art known intermediates have been used such as, e.g. 3-cyanopropyl bromide, tetrahydrofurfuryl methanesulfonate, 3-hydroxypropyl bromide, 2-methoxyethyl bromide, 3-methoxypropyl chloride, (trans)-4-(aminomethyl)-1-[2-(1,3-dioxolan-2-yl)ethyl]-3-piperidinol (described as intermediate 8 in WO-00/37461), 1-chloro-3-(1-methylethoxy)-propane, 2-(3-chloropropyl)-2-methyl-1,3-dioxolane, 2-(2-bromoethyl)-1,3-dioxolane, methyl 4-bromobutanoate, 2-chloro-acetonitrile, 2-(2-chloroethoxy)-ethanol, N-(2-chloroethyl)-methanesulfonamide, and N-[3-[(methylsulfonyl)oxy]propyl]-methanesulfonamide, 1-(2-chloroethyl)-1,3-dihydro-3-(1-methylethyl)-2H-imidazol-2-one, ethyl (3-chloropropyl)-carbamic acid ester.

B. Preparation of the Final Compounds

Example B.1

A mixture of intermediate (45) (0.05 mol) in HCl/2-propanol (6N) (0.24 mol) and 2-propanol (300 ml) was refluxed and stirred for 1 hour. The reaction mixture was cooled and the solvent was evaporated. The residue was taken up in DCM and washed with a 5 % H$_2$O/NaOH solution. The organic layer was dried, filtered and the solvent was evaporated. The residue was purified by column chromatography over silica gel (eluent: CH$_2$Cl$_2$(CH$_3$OH/NH$_3$) 93/7). The product fractions were collected and the solvent was evaporated. The residue was crystallised from DIPE, yielding 7.5 g of compound (117) (mp. 160° C.).

Example B.2

A mixture of compound (157) (0.0156 mol), 1-chloro-3-methoxy-propane (0.0234 mol) and potassium carbonate (0.0312 mol) in acetonitrile (85 ml) was stirred and refluxed for 15 hours then brought to room temperature, poured out into water and extracted with ethyl acetate. The organic layer was separated, dried, filtered, and the solvent was evaporated till dryness. The residue was purified by column chromatography over silica gel (eluent: CH$_2$Cl$_2$/CH$_3$OHONH$_4$OH 94/6/0.1). The pure fractions were collected and the solvent was evaporated. The residue was crystallized from a mixture of isopropyl ether and 2-propanone. The precipitate was filtered off and dried, yielding 2.29 g of compound (2) (mp. 109° C.).

Example B.3

A mixture of compound (8) (0.01 mol) and butanal in methanol (150 ml) was hydrogenated with platinum-on-carbon (5%, 1 g) as a catalyst in the presence of thiophene solution (1 ml). After uptake of hydrogen (1 equivalent), the catalyst was filtered off and the filtrate was evaporated. The residue was partitioned between water and DCM. The organic layer was separated, dried, filtered and the solvent was evaporated. The residue was crystallized from DIPE. The precipitate was filtered off and dried, yielding 2.94 g of compound (7) (mp. 127° C.).

Example B.4 a) Preparation of

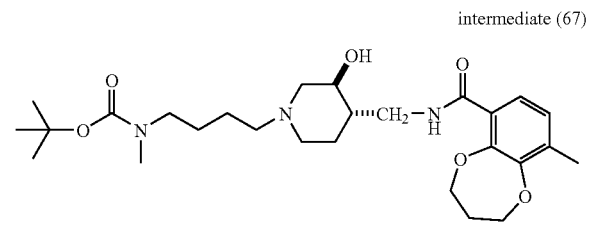

intermediate (67)

A mixture of compound (157) (0.0244 mol), 1,1-dimethylethyl methyl-(4-oxobutyl)-carbamic acid ester (0.0244 mol) and palladium-on-carbon (10%, 1.86 g) in thiophene solution (1.86 ml), methanol (186 ml) and THF (10 ml) was hydrogenated for 45 minutes under a 2 bar (0.2 M.Pa) pressure of hydrogen, then filtered over celite. The filtrate was evaporated till dryness. The residue was purified by column chromatography over silica gel (eluent: $CH_2Cl_2/CH_3OH/NH_4OH$ 96/4/0.1 to 95/5/0.5). The pure fractions were collected and the solvent was evaporated, yielding 4.8 g of intermediate (67).

b) A mixture of intermediate (67) (0.0095 mol) in 2-propanol (85ml) and HCl (5-6N, 10.3 ml) was stirred at 50° C. for 2 hours, then cooled to room temperature and the solvent was evaporated. The residue was taken up in water, basified with potassium carbonate and extracted with ethyl acetate. The organic layer was separated, dried, filtered, and the solvent was evaporated till dryness, and converted into the ethanedioic acid salt, yielding compound (4) (mp. 120° C.).

Example B.5

A mixture of intermediate (15) (0.01 mol) in DCM (80 ml) was stirred at 0° C. Triethylamine (0.01 mol) was added at 0° C. Ethyl chlorocarbonate (0.01 mol) was added dropwise at 0° C. The mixture was stirred at 0° C. for 30 minutes. A mixture of intermediate (30) (0.01 mol) in DCM (20 ml) was added at 0° C. The mixture was brought to room temperature an then stirred at room temperature for 30 minutes. The mixture was washed with water, a 5% aqueous NaOH solution and again with water. The organic layer was separated, dried, filtered and the solvent was evaporated. The residue was solidified in DIPE. The precipitate was filterd off, washed and dried, yielding 2.95 g of compound (16) (mp. 115° C.).

Example B.6

Sodium cyanoborohydride (0.02 mol) was added at room temperature to a solution of compound (157) (0.0134 mol) and butanal (0.02 mol) in methanol (80 ml) under nitrogen flow. The mixture was stirred for 1 hour. Water was added. The mixture was extracted with ethyl acetate. The organic layer was separated, dried, filtered and the solvent was evaporated till dryness. The residue was purified by column chromatography over silica gel (eluent: $CH_2Cl_2/CH_3OH/NH_4OH$ 97/3/0.3). The pure fractions were collected and the solvent was evaporated. The residue was crystallized from petroleum ether. The precipitate was filtered off and dried, yielding 1.59 g of compound (1) (mp. 127° C.).

Example B.7 a) Preparation of

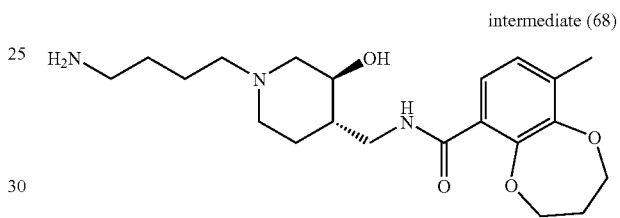

intermediate (68)

Compound (148) (0.013 mol) in $CH_3OH/NH_3$ (300 ml) was hydrogenated with Raney Nickel (1 g) as a catalyst. After uptake of $H_2$ (2 equiv.) the catalyst was filtered off and the filtrate was evaporated, yielding 5.1 g (100%) of intermediate (68). b) Methanesulfonyl chloride (1.16 ml) was added dropwise at room temperature to a solution of intermediate (68) (0.013 mol) and triethylamine (0.026 mol) in DCM (120 ml). After 3 hours, methanesulfonyl chloride (0.4 ml) was added and the mixture was stirred overnight. The mixture was washed with water, the organic layer was dried, filtered and the solvent was evaporated. The residue was purified by flash column chromatography over silica gel (eluent: $CH_2Cl_2/$ $(CH_3OH/NH_3)$ 99/1, 98/2, 97/3). The product fractions were collected and the solvent was evaporated. The residue was crystallised from $DIPE/CH_3CN$, filtered off, washed and dried, yielding 1.9 g of compound (107) (mp. 124° C.).

Example B.8

Ethyl chlorocarbonate (0.005 mol, 0° C.) was added dropwise to a mixture of compound (149) (0.0047 mol), triethylamine (0.01 mol) in DCM (50 ml) at a temperature of 0° C. The reaction mixture was stirred at 0° C. for 1 hour and the solvent was evaporated. The residue was taken up in THF. The precipitate was filtered and the filtrate was stirred at 5° C. THF/$NH_3$ (100 ml) was added to the solution. The reaction mixture was stirred at room temperature for 16 hours and the solvent was evaporated. The residue was taken up in DCM and washed with water. The organic layer was dried, filtered off and the solvent was evaporated. The residue was purified by column chromatography over silica gel (eluent: $CH_2Cl_2/$ $(CH_3OH/NH_3)$ 93/7). The product fractions were collected and the solvent was evaporated. The residue was crystallised from DIPE, filtered off, washed and dried, yielding 0.36 g of compound (109) (mp. 160° C.).

Example B.9

A mixture of compound (150) (0.0122 mol) and potassium hydroxide (0.0331 mol) in ethanol (180 ml) was stirred and refluxed for 4 days, then cooled to room temperature. The solvent was evaporated. The residue was taken up in water and ethyl acetate. The mixture was extracted with ethyl acetate. The organic layer was separated, dried, filtered, and the solvent was evaporated. The residue was purified by column chromatography over silica gel (eluent: $CH_2Cl_2$/$CH_3OH$/$NH_4OH$ 89/11/1 to 85/15/1), yielding 0.832 g of compound (128).

Example B.10 a) Preparation of

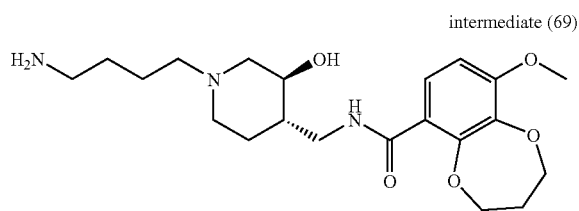

intermediate (69)

A mixture of compound (150) (0.006 mol) and Raney Nickel (2.4g) in $NH_4OH$/$CH_3OH$ (50 ml) was hydrogenated at room temperature for 5 hours under a 3 bar (0.3 M.Pa) pressure, then filtered over celite. The filtrate was evaporated till dryness, yielding 2.5 g of intermediate (69).

b) A mixture of intermediate (69) (0.0061 mol) and 2-chloro-3-methyl-pyrazine (0.0073 mol) was stirred at 100° C. overnight, then cooled to room temperature and purified by column chromatography over silica gel (eluent: $CH_2Cl_2$/$CH_3OH$/$NH_4OH$ 90/10/1). The pure fractions were collected and the solvent was evaporated. The residue was dried, yielding 0.463 g of compound (130).

Example B.11

A mixture of compound (151) (0.0027 mol) in sulfuric acid (20 ml) and water (2 ml) was stirred at 0° C. then, at room temperature for 24 hours. The reaction mixture was poured out into ice and added to aqueous $NH_3$ at 0° C. The mixture was extracted with DCM, dried and the solvent was evaporated. The residue was crystallised from ACN, filtered off and dried, yielding 0.394 g of compound (140) (mp. 180° C.).

Example B.12

Potassium hydroxide (0.0082 mol) was dissolved in ethanol (40 ml), compound (158) (0.00306 mol) was added and the reaction mixture was stirred and refluxed for 5 days. The solvent was evaporated and the residue was partitioned between DCM and a 2% aqueous NaOH solution and extracted with DCM (4 times). The organic layer was dried and the solvent was evaporated. The residue was purified by flash column chromatography (Biotage) over silica gel (eluent 1: pure $CH_2Cl_2$, eluent 2: $CH_2Cl_2$/($CH_3OH$/$NH_3$) from 97/3 to 90/10). The two product fractions were collected and the solvent was evaporated yielding 0.41 g of compound (145) (mp.131° C.) and 0.13 g of compound (146) (mp. 154° C.).

Example B.13 a) Preparation of

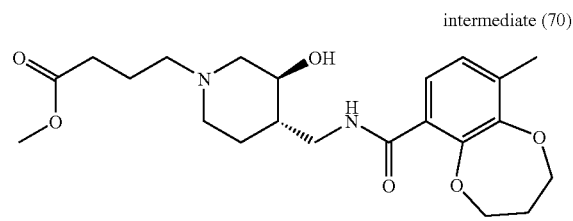

intermediate (70)

A mixture of compound (152) (0.036 mol), 4-bromo-butanoic acid, methyl ester (0.047 mol), triethylamine (0.09 mol) in DMF (200 ml) was stirred at 75° C. for 16 hours. The reaction mixture was cooled, poured out into water and extracted with toluene. The organic layer was dried, filtered off and the solvent was evaporated. The residue was purified over silica gel on a glass filter (eluent: $CH_2Cl_2$/($CH_3OH$/$NH_3$) 97/3). The product fractions were collected and the solvent was evaporated, yielding 12.4 g of intermediate (70).

b) A mixture of intermediate (70) (0.0295 mol) in water (50 ml) was stirred at 95° C. for two days. The reaction mixture was cooled and the solvent was evaporated, yielding 8.5 g of compound (149).

Table F-1 lists the compounds that were prepared according to one of the above Examples.

TABLE F-1

| Co. No. | Ex. No. | Structure | Physical data |
|---|---|---|---|
| 1 | B.6 | 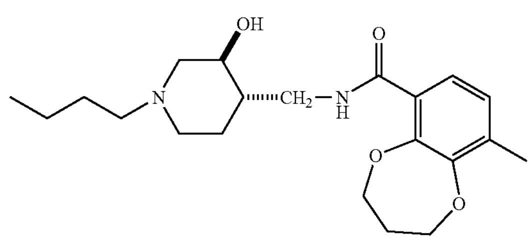 | (trans); mp. 127° C. |

TABLE F-1-continued

| Co. No. | Ex. No. | Structure | Physical data |
|---|---|---|---|
| 2 | B.2 | 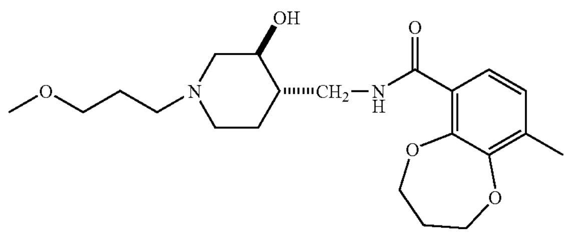 | (trans); mp. 109° C. |
| 3 | B.2 | 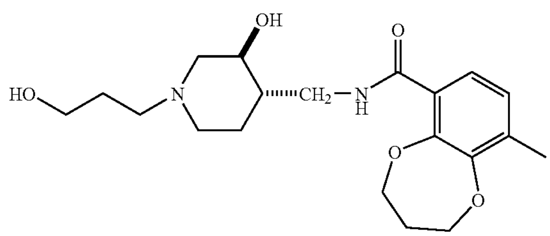 | (trans); mp. 130° C. |
| 4 | B.4 | 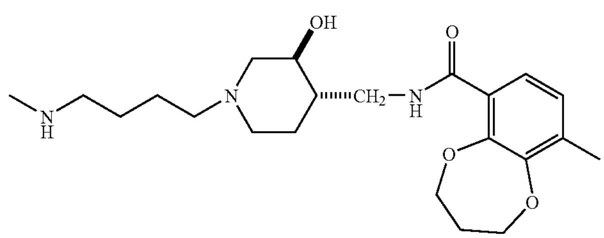 | (trans); .ethanedioate (1:2); mp. 120° C. |
| 5 | B.2 | 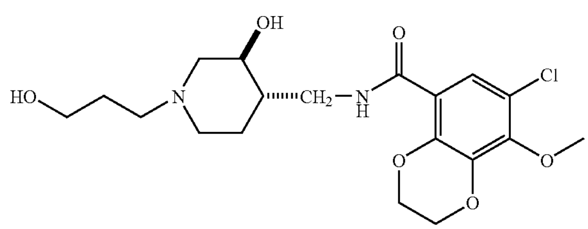 | (trans); mp. 133° C. |
| 6 | B.2 | 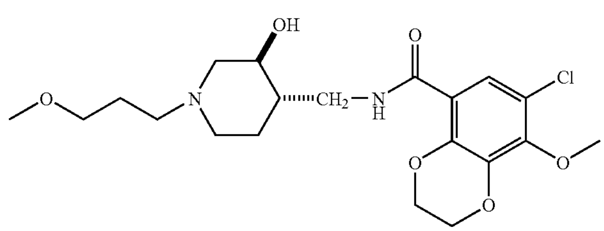 | (trans); •H$_2$O (1:1); mp. 84-86° C. |
| 7 | B.3 | 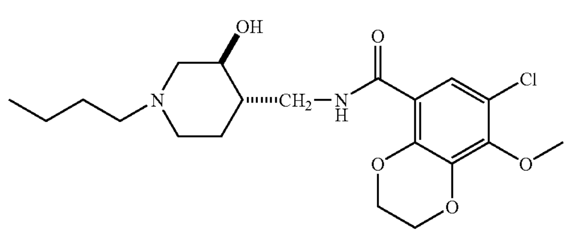 | (trans); mp. 127° C. |

TABLE F-1-continued

| Co. No. | Ex. No. | Structure | Physical data |
|---|---|---|---|
| 8 | B.1 | 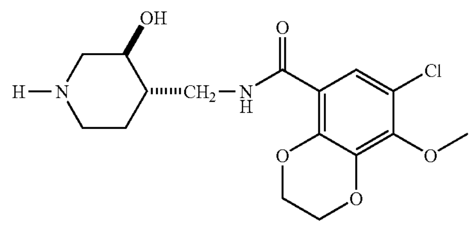 | (trans); •HCl (1:1); mp. 160-162° C. |
| 9 | B.2 | 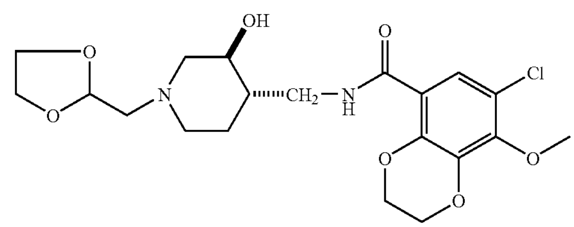 | (trans); mp. 114° C. |
| 10 | B.2 | 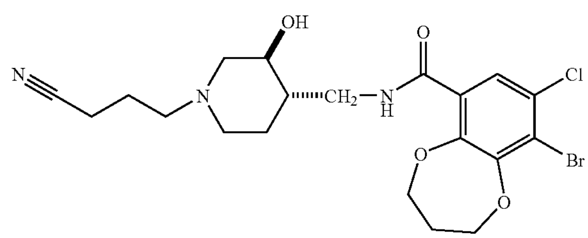 | (trans); mp. 136° C. |
| 11 | B.1 | 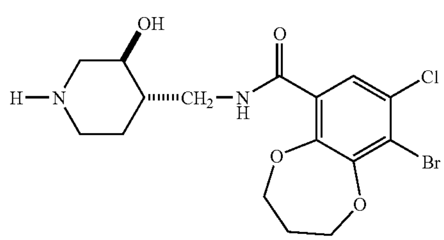 | (trans); •HCl (1:1); mp. 206° C. |
| 12 | B.1 | 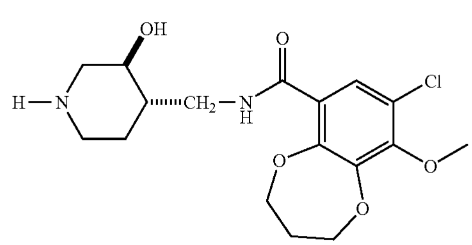 | (trans); mp. >90° C.; •ethanedioate (1:1)•2-propanolate (1:1) |
| 13 | B.2 | 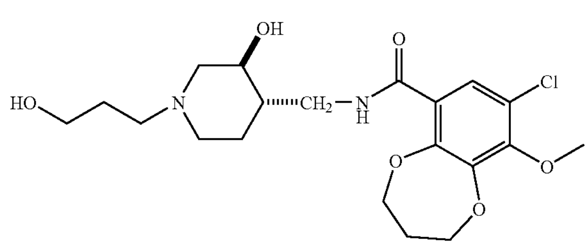 | (trans); mp. 99° C. |

TABLE F-1-continued

| Co. No. | Ex. No. | Structure | Physical data |
|---|---|---|---|
| 14 | B.2 | 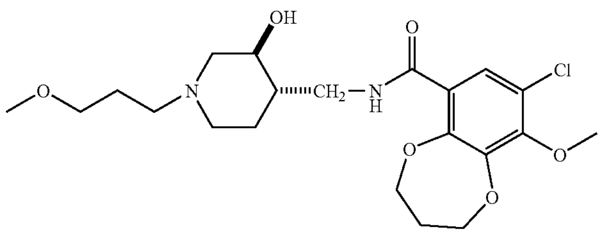 | (trans); mp. 111° C. |
| 15 | B.2 | 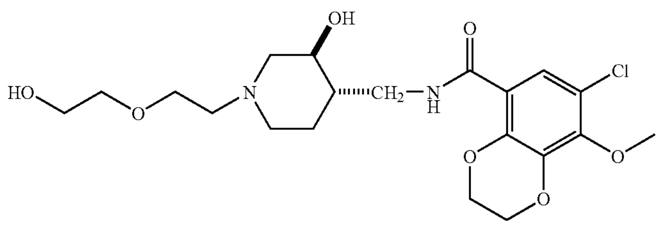 | (trans); •ethanedioate (1:1); mp. >100° C. |
| 16 | B.5 | 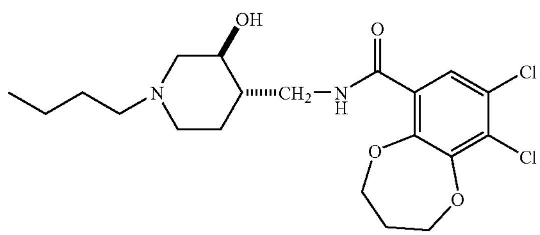 | (trans); mp. 115° C. |
| 17 | B.3 | 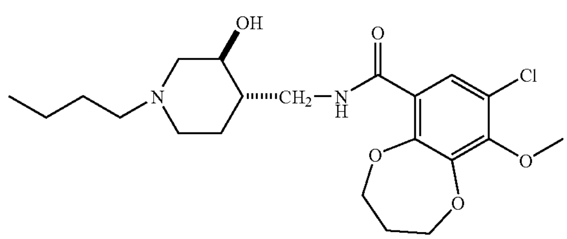 | (trans); mp. 100° C. |
| 18 | B.2 | 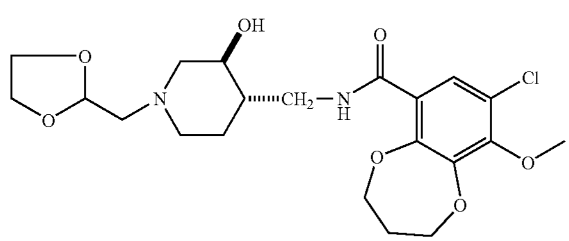 | (trans); mp. 116° C. |
| 19 | B.5 | 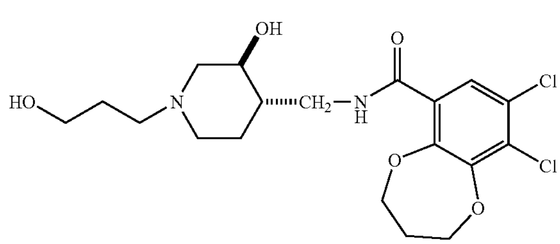 | (trans); mp. 136° C. |

TABLE F-1-continued

| Co. No. | Ex. No. | Structure | Physical data |
|---|---|---|---|
| 20 | B.1 | 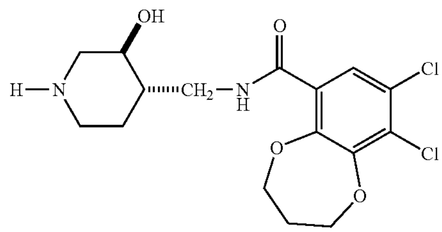 | (trans); •HCl (1:1); mp. 173° C. |
| 21 | B.5 | 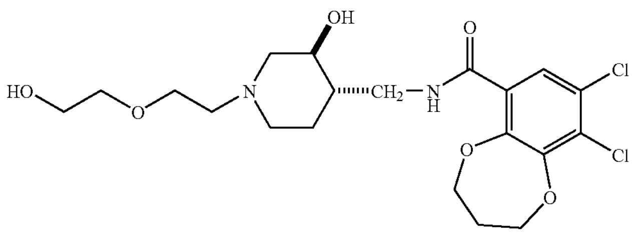 | (trans); •HCl (1:1)•H₂O (1:1); mp. 129° C. |
| 22 | B.5 | 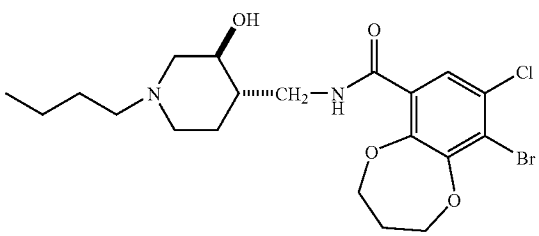 | (trans); mp. 140° C. |
| 23 | B.2 | 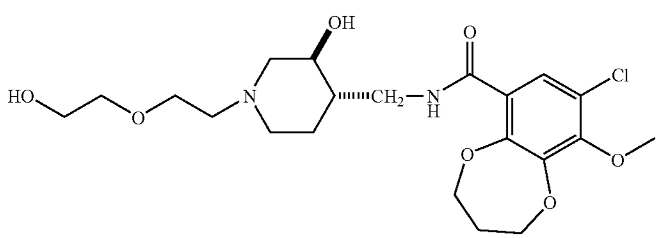 | (trans); mp. >70° C. |
| 24 | B.5 | 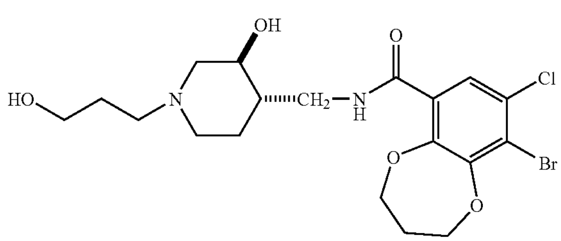 | (trans); mp. 139° C. |
| 25 | B.5 | 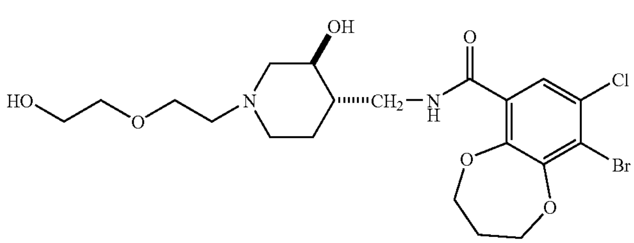 | (trans); •HCl (1:1); mp. 159° C. |

TABLE F-1-continued

| Co. No. | Ex. No. | Structure | Physical data |
|---|---|---|---|
| 26 | B.5 | 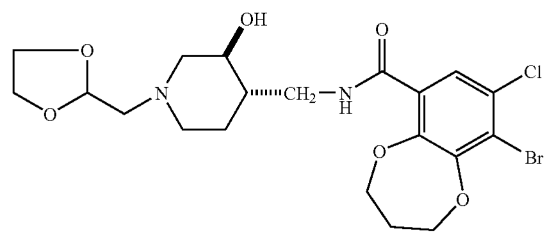 | (trans); mp. 123° C. |
| 27 | B.2 | 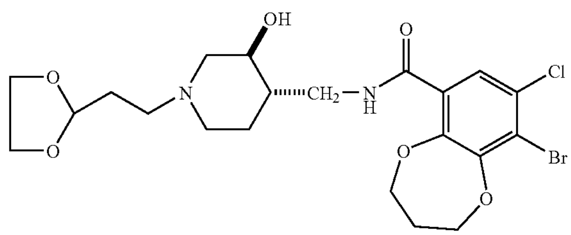 | (trans); mp. 138° C. |
| 28 | B.2 | 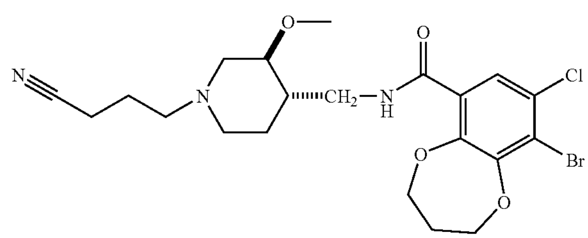 | (trans); •ethanedioate (1:1); mp. 204° C. |
| 29 | B.2 | 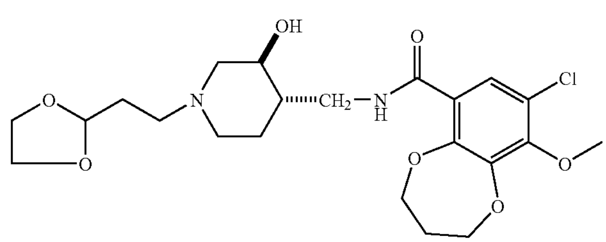 | (trans); mp. 132-134° C. |
| 30 | B.2 | 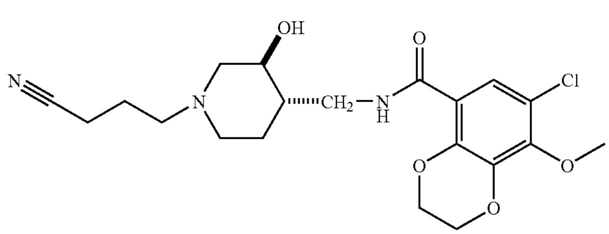 | (trans); mp. 96° C. |
| 31 | B.2 | 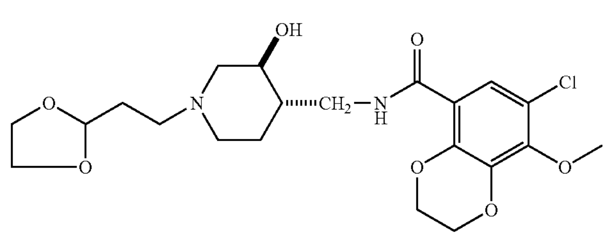 | (trans); •H$_2$O (1:1); mp. 80° C. |

TABLE F-1-continued

| Co. No. | Ex. No. | Structure | Physical data |
|---|---|---|---|
| 32 | B.2 | 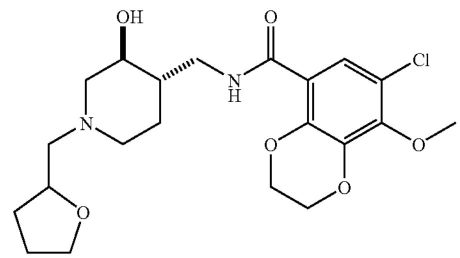 | (trans); mp. 104° C. |
| 33 | B.2 | 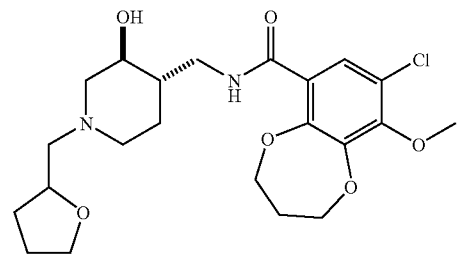 | (trans); mp. >70° C. |
| 34 | B.2 | 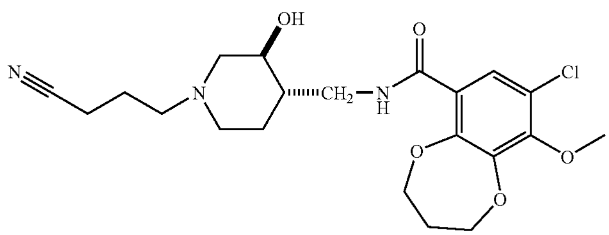 | (trans); mp. 107-108° C. |
| 35 | B.1 | 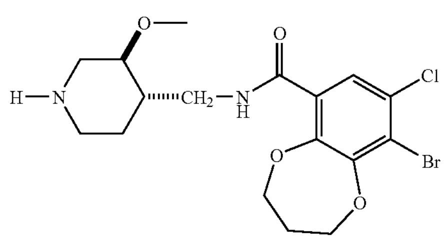 | (trans); •ethanedioate (1:1)•H₂O (1:1); mp. 157.7-182.2° C. |
| 36 | B.4 | 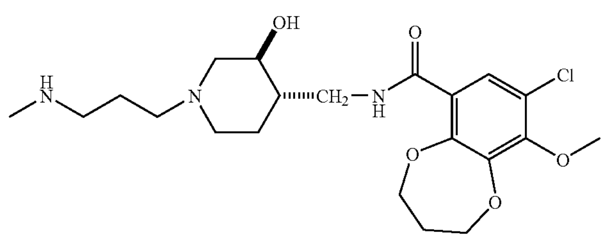 | (trans); •HCl (1:2)•H₂O (1:1); mp. 140° C. |
| 37 | B.5 | 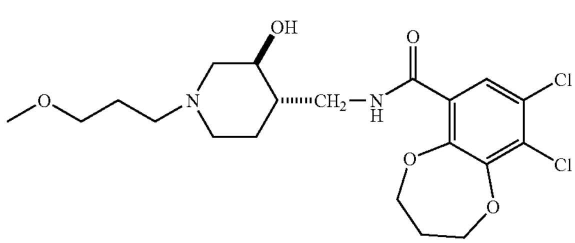 | (trans); •ethanedioate (1:1); mp. 204° C. |

TABLE F-1-continued

| Co. No. | Ex. No. | Structure | Physical data |
|---|---|---|---|
| 38 | B.5 | 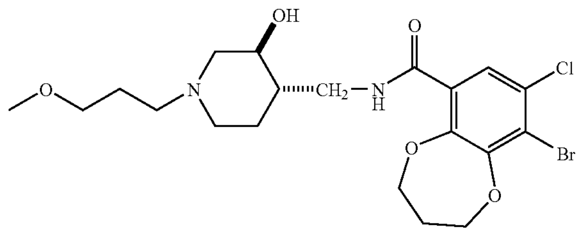 | (trans); •ethanedioate (1:1); mp. 206° C. |
| 39 | B.2 | 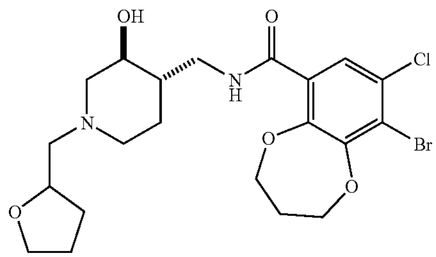 | (trans); mp. 112° C. |
| 40 | B.4 | 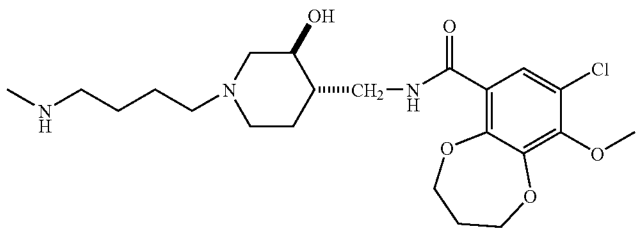 | (trans); •ethanedioate (1:2); mp. 100° C. |
| 41 | B.2 | 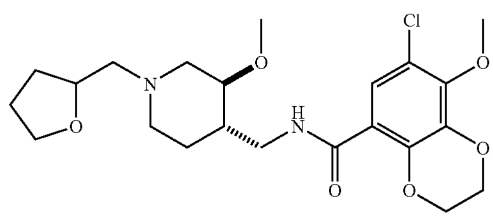 | (trans); •ethanedioate (1:1); mp. 167° C. |
| 42 | B.4 | 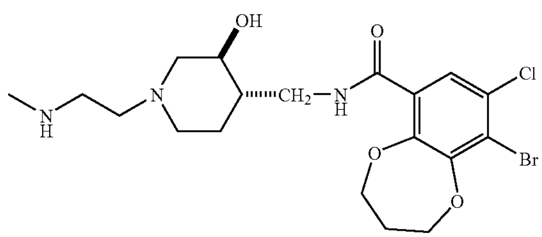 | (trans); •ethanedioate (1:2); mp. 256° C. |
| 43 | B.4 | 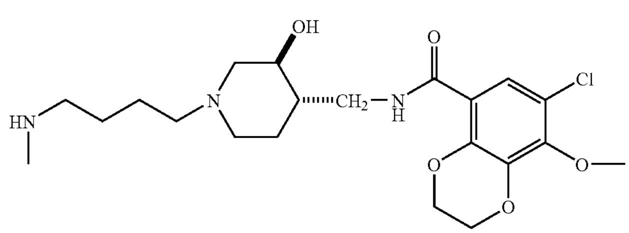 | (trans); •ethanedioate (1:2); mp. 126° C. |

TABLE F-1-continued

| Co. No. | Ex. No. | Structure | Physical data |
|---|---|---|---|
| 44 | B.4 | 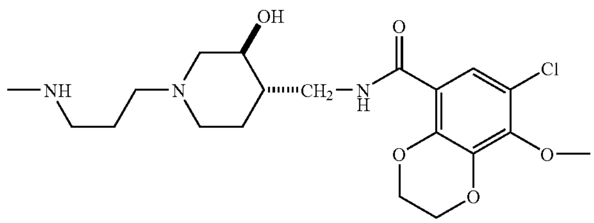 | (trans); •ethanedioate (1:2); mp. >110° C. |
| 45 | B.2 | 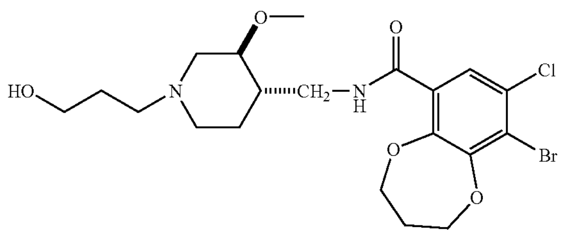 | (trans); •ethanedioate (1:1); mp. 175-177° C. |
| 46 | B.2 | 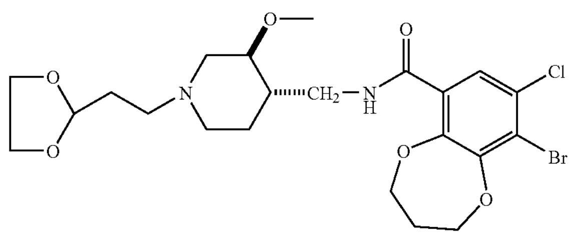 | (trans); •ethanedioate (1:1); mp. 195° C. |
| 47 | B.1 | 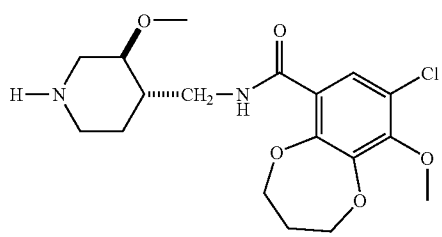 | (trans); •ethanedioate (2:1); mp. >230° C. |
| 48 | B.4 | 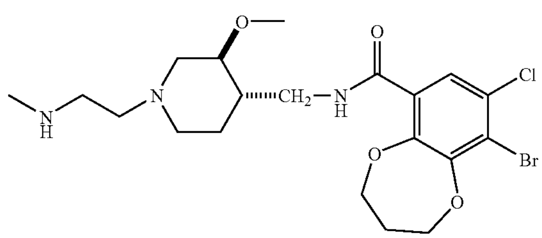 | (trans); •ethanedioate (1:2); mp. 220° C. |
| 49 | B.1 | 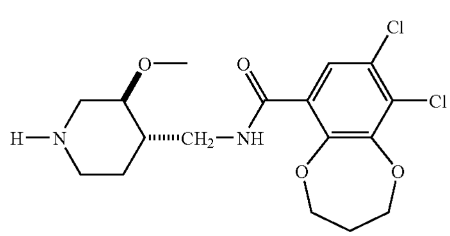 | (trans); •HCl (1:1); mp. 220° C. |

TABLE F-1-continued

| Co. No. | Ex. No. | Structure | Physical data |
|---|---|---|---|
| 50 | B.2 | 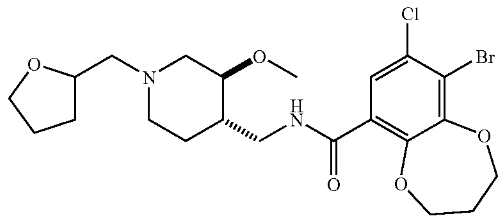 | (trans); •ethanedioate (1:1); mp. 204° C. |
| 51 | B.2 | 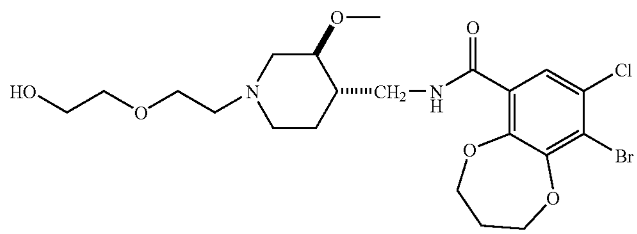 | (trans); •ethanedioate (1:1); mp. 142° C. |
| 52 | B.1 | 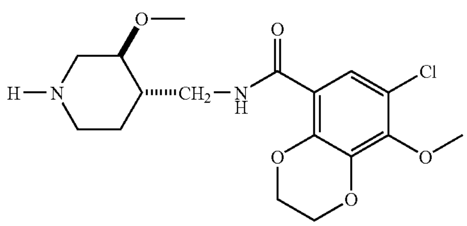 | (trans); •ethanedioate (2:1); mp. 174.5-195.7° C. |
| 53 | B.2 | 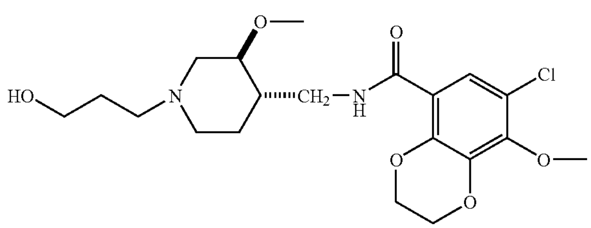 | (trans); •ethanedioate (1:1)•H$_2$O (1:1); mp. 130° C. |
| 54 | B.2 | 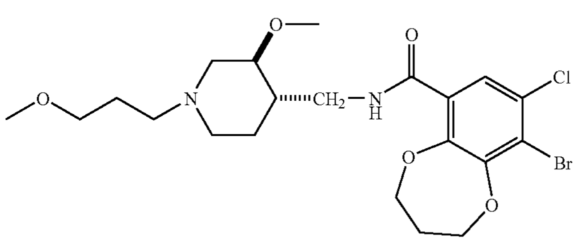 | (trans); •ethanedioate (1:1); mp. 203° C. |
| 55 | B.2 | 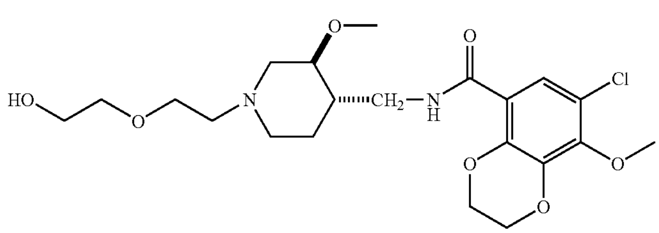 | (trans); •ethanedioate (1:1); mp. 197° C. |

TABLE F-1-continued

| Co. No. | Ex. No. | Structure | Physical data |
|---|---|---|---|
| 56 | B.2 | 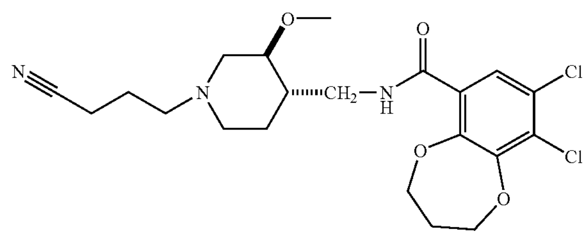 | (trans); •ethanedioate (1:1); mp. 190° C. |
| 57 | B.2 | 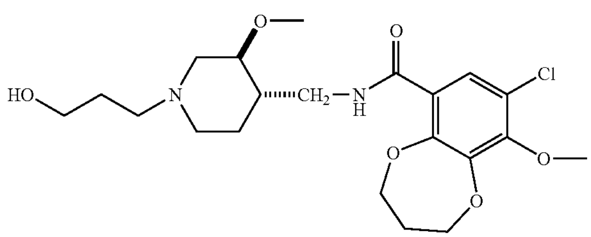 | (trans); •ethanedioate (1:1); mp. 171° C. |
| 58 | B.3 | 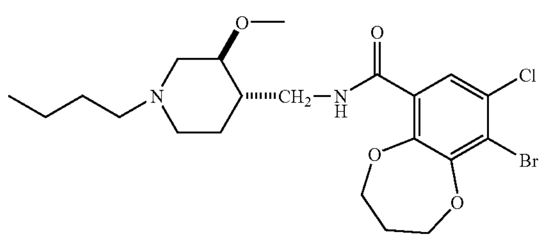 | (trans); •ethanedioate (1:1); mp. 222° C. |
| 59 | B.2 | 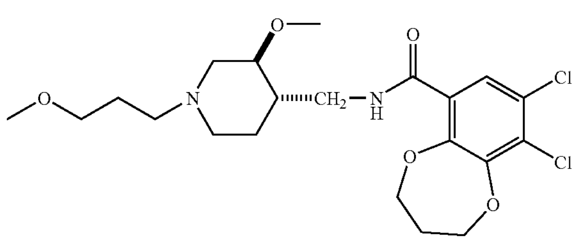 | (trans); •ethanedioate (1:1); mp. 192° C. |
| 60 | B.2 | 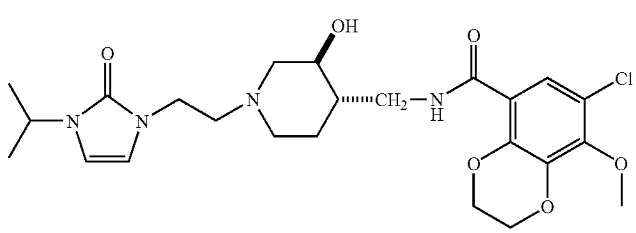 | (trans); •(E)-2-butenedioate (1:1)•H$_2$O (1:1); mp. 232.1-234.3° C. |
| 61 | B.4 | 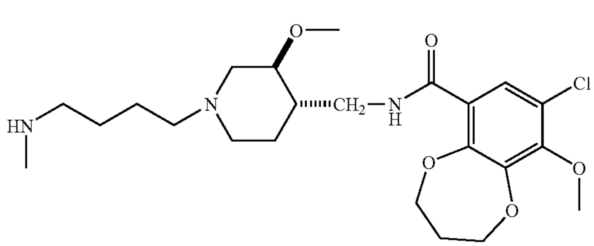 | (trans); •ethanedioate (1:2); mp. >90° C. |

TABLE F-1-continued
| Co. No. | Ex. No. | Structure | Physical data |
|---|---|---|---|
| 62 | B.4 | 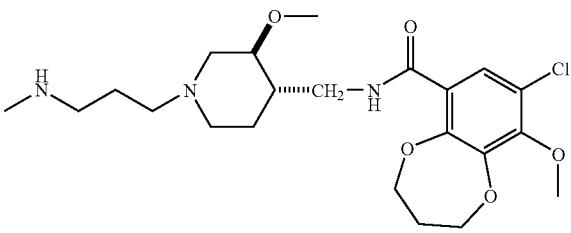 | (trans); •ethanedioate (1:2); mp. >180° C. |
| 63 | B.4 | 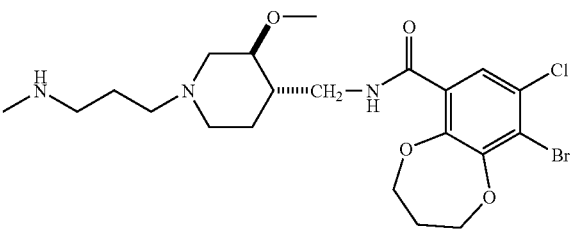 | (trans); •HCl (1:2)•H₂O (1:1); mp. >140° C. |
| 64 | B.4 | 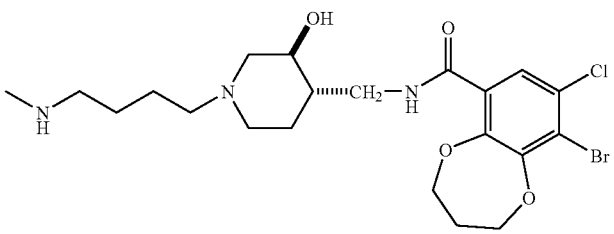 | (trans); mp. 130° C. |
| 65 | B.4 | 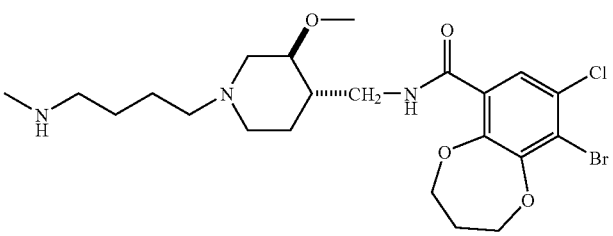 | (trans); •HCl (1:2); mp. 230° C. |
| 66 | B.2 | 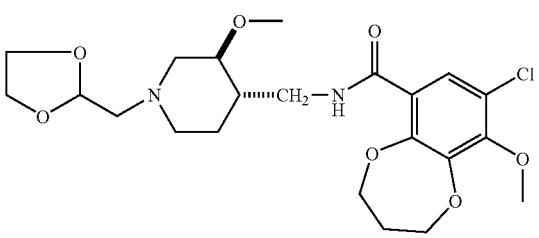 | (trans); mp. 116° C. |
| 67 | B.2 | 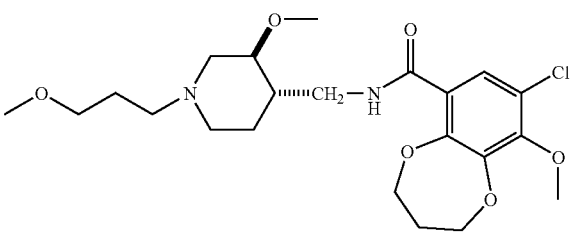 | (trans); •ethanedioate (1:1); mp. 199° C. |

TABLE F-1-continued

| Co. No. | Ex. No. | Structure | Physical data |
|---|---|---|---|
| 68 | B.2 | 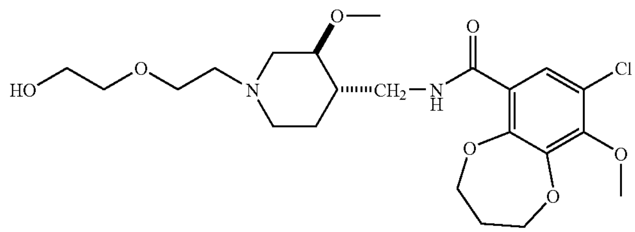 | (trans); •ethanedioate (1:1); mp. 159° C. |
| 69 | B.2 | 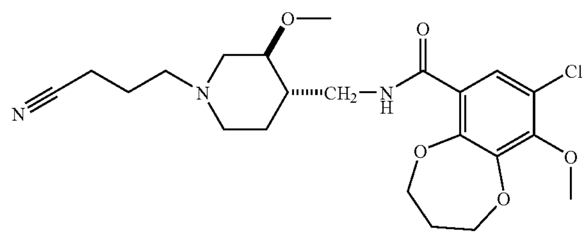 | (trans); •ethanedioate (1:1); mp. 182° C. |
| 70 | B.2 | 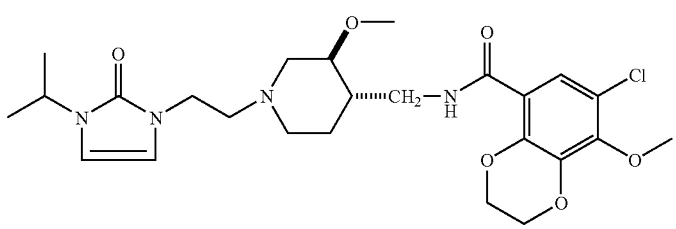 | (trans); •(E)-2-butenedioate (1:3); mp. 57.1-64.3° C. |
| 71 | B.3 | 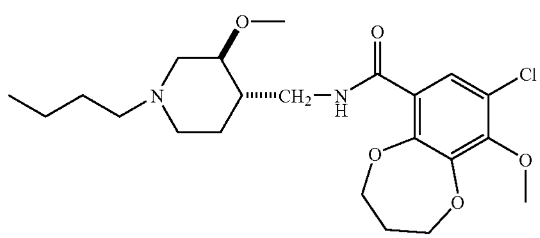 | (trans); •ethanedioate (1:1); mp. 214° C. |
| 72 | B.2 | 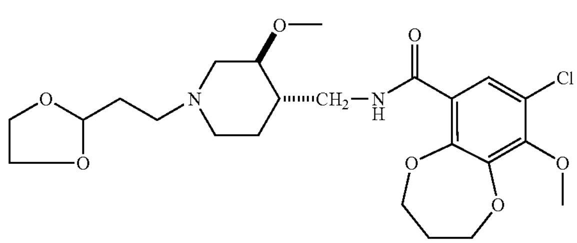 | (trans); •ethanedioate (1:1); mp. 186° C. |
| 73 | B.2 | 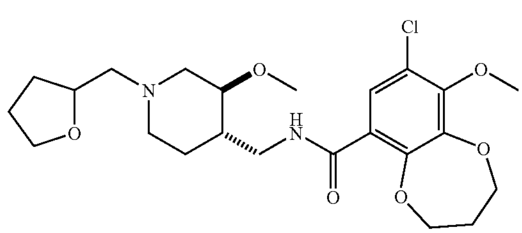 | (trans); •ethanedioate (1:1); mp. 192° C. |

TABLE F-1-continued

| Co. No. | Ex. No. | Structure | Physical data |
|---|---|---|---|
| 74 | B.4 | 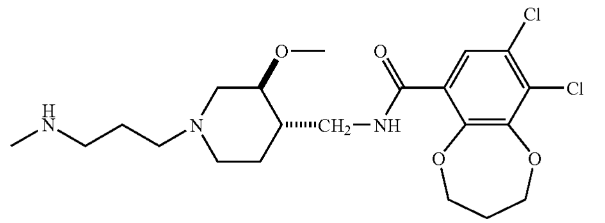 | (trans); •HCl (1:2); mp. 210° C. |
| 75 | B.2 | 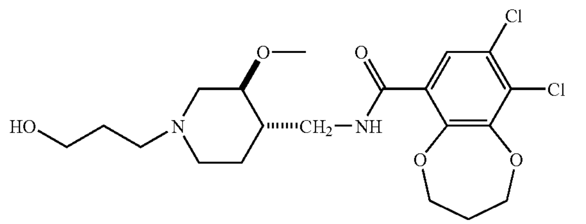 | (trans); •ethanedioate (1:1) H₂O (1:1); mp. 149° C. |
| 76 | B.2 | 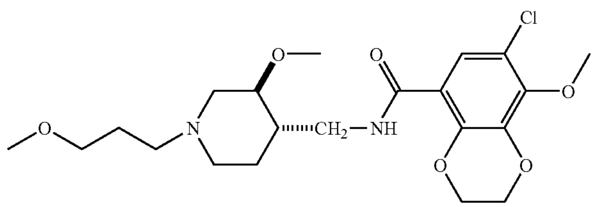 | (trans); •ethanedioate (1:1); mp. 195° C. |
| 77 | B.3 | 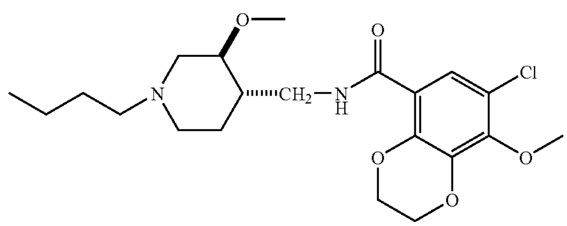 | (trans); •ethanedioate (1:1); mp. 150° C. |
| 78 | B.4 | 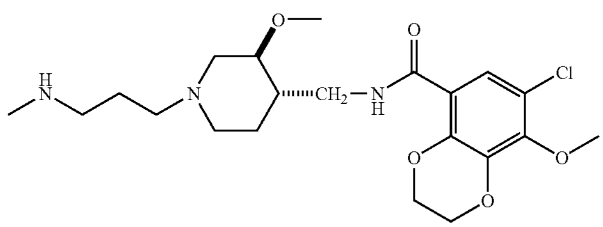 | (trans); •ethanedioate (1:2); mp. 132° C. |
| 79 | B.2 | 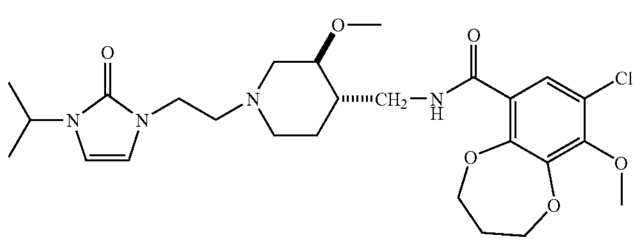 | (trans); •(E)-2-butenedioate (1:1); mp. 60° C. |

TABLE F-1-continued

| Co. No. | Ex. No. | Structure | Physical data |
|---|---|---|---|
| 80 | B.4 | 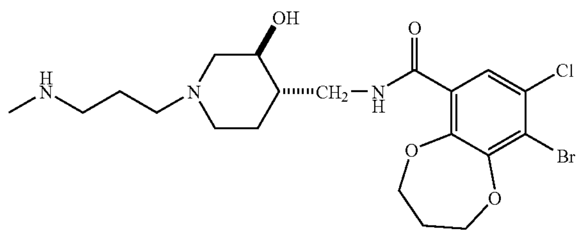 | (trans); •HCl (1:2)•H₂O (1:1); mp. 152° C. |
| 81 | B.3 | 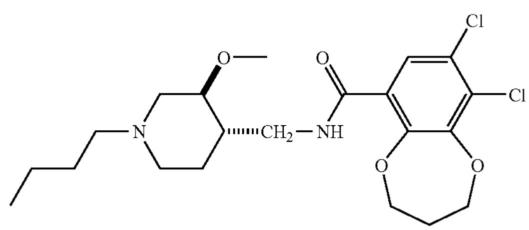 | (trans); •ethanedioate (1:1); mp. 216° C. |
| 82 | B.2 | 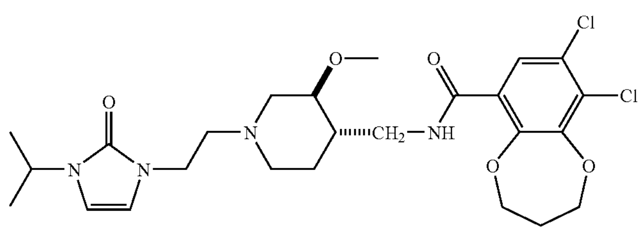 | (trans); •ethanedioate (1:1); mp. 156° C. |
| 83 | B.4 | 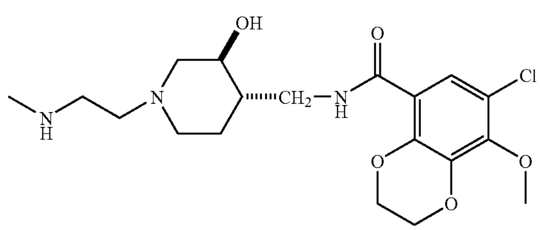 | (trans); •ethanedioate (1:2); mp. 230° C. |
| 84 | B.4 | 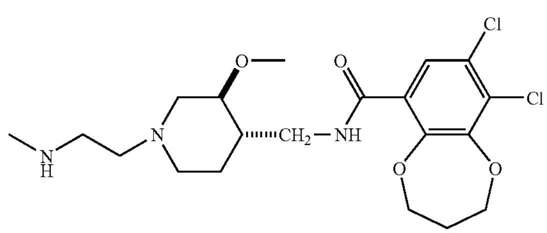 | (trans); •ethanedioate (1:1); mp. 171° C. |
| 85 | B.4 | 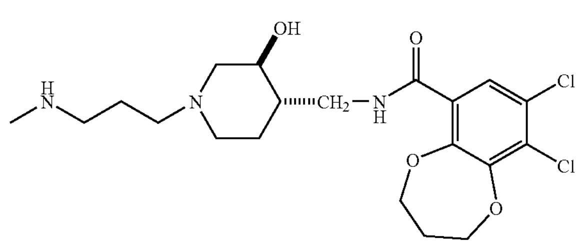 | (trans); •ethanedioate (1:2); mp. 228° C. |

TABLE F-1-continued

| Co. No. | Ex. No. | Structure | Physical data |
|---|---|---|---|
| 86 | B.4 | 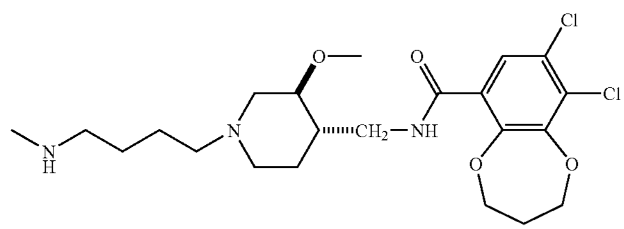 | (trans); •ethanedioate (1:2)•H$_2$O (1:1); mp. >120° C. |
| 87 | B.2 | 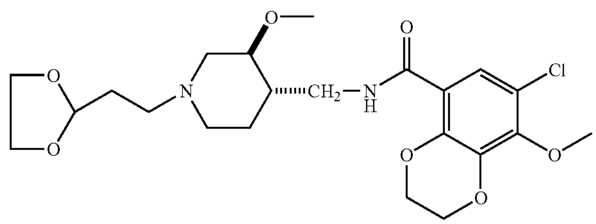 | (trans); •ethanedioate (1:1); mp. 190° C. |
| 88 | B.2 | 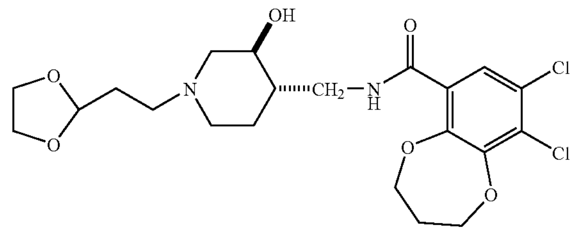 | (trans); •ethanedioate (1:1); mp. 200° C. |
| 89 | B.2 | 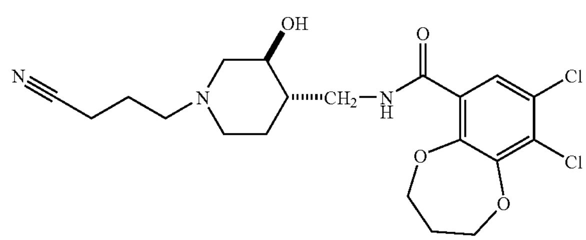 | (trans); mp. 128° C. |
| 90 | B.4 | 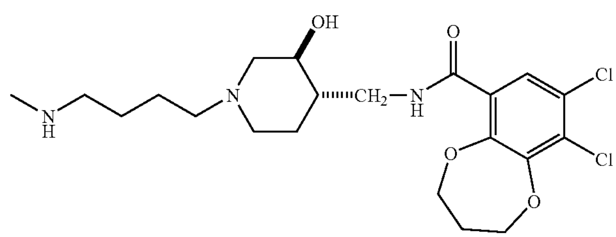 | (trans); •ethanedioate (1:2); mp. 150° C. |
| 91 | B.2 | 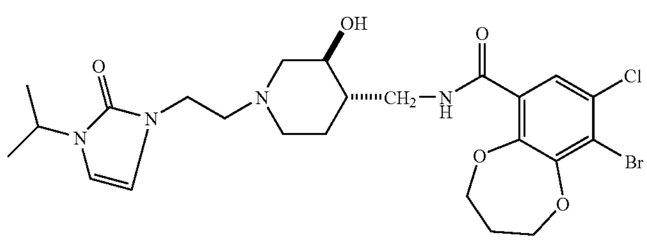 | (trans); mp. 174° C. |

TABLE F-1-continued

| Co. No. | Ex. No. | Structure | Physical data |
|---|---|---|---|
| 92 | B.4 | 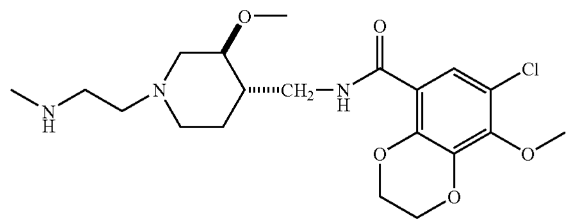 | (trans); •ethanedioate (2:5); mp. 194° C. |
| 93 | B.2 | 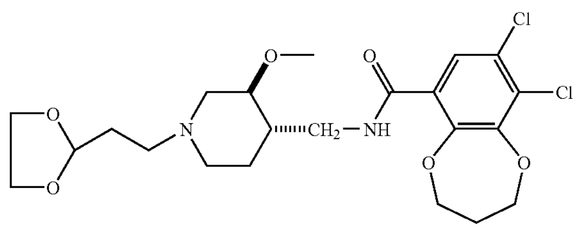 | (trans); •ethanedioate (1:1); mp. 178° C. |
| 94 | B.5 | 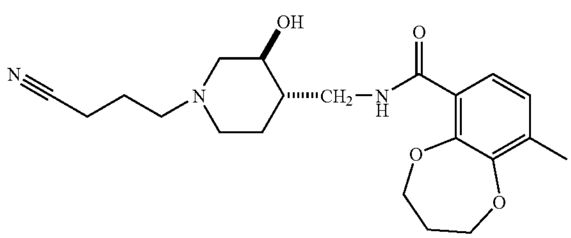 | (trans); mp. 127° C. |
| 95 | B.5 | 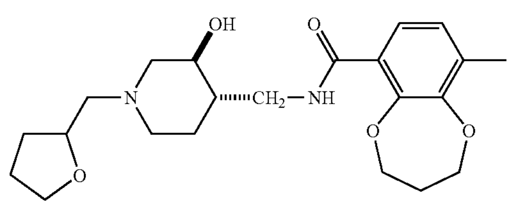 | (trans); mp. 60° C. |
| 96 | B.2 | 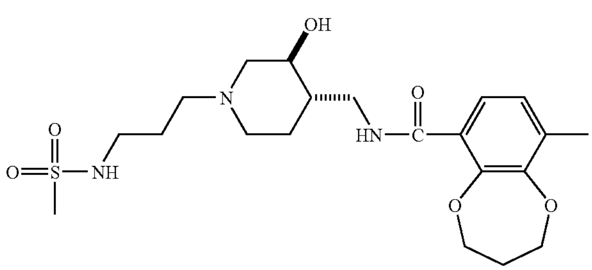 | (3S-trans); •ethanedioate (1:1); mp. 151° C.; $[\alpha]^{20,D} = -9.97°$ (c = 24.08 mg/5 ml in methanol) |
| 97 | B.1 | 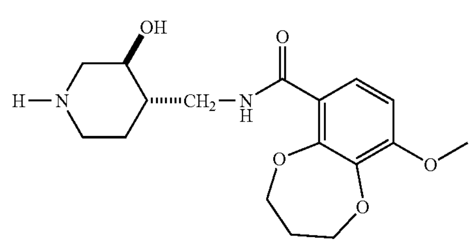 | (trans); •HCl (1:1); mp. 130° C. |

TABLE F-1-continued

| Co. No. | Ex. No. | Structure | Physical data |
|---|---|---|---|
| 98 | B.5 | 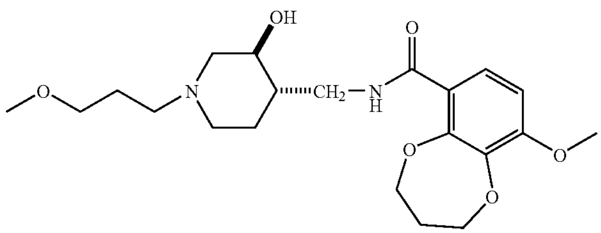 | (trans); mp. 118° C. |
| 99 | B.2 | 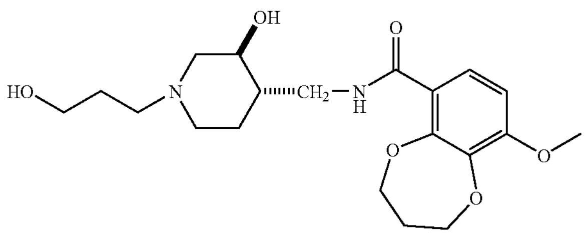 | (trans); mp. 145° C. |
| 100 | B.5 | 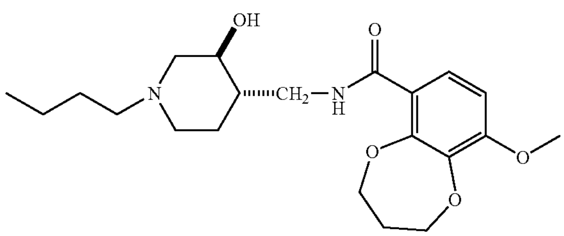 | (trans); mp. 123° C. |
| 101 | B.5 | 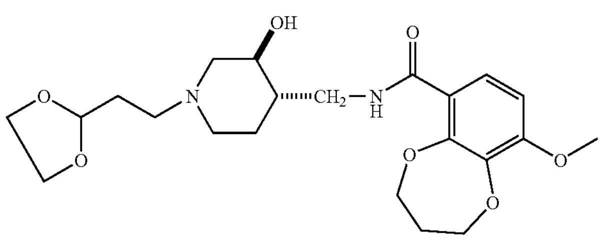 | (trans); mp. 150° C. |
| 102 | B.4 | 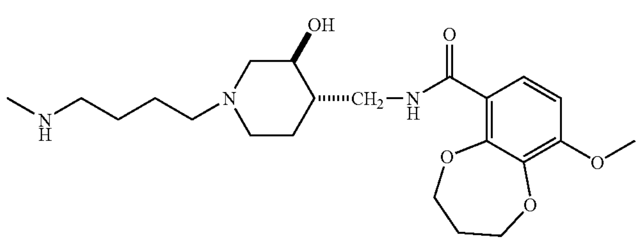 | (trans); •HCl (1:2) H$_2$O (1:1); mp. 135° C. |
| 103 | B.4 | 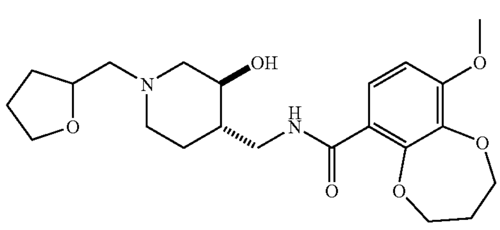 | (trans); •ethanedioate (1:1); mp. 122° C. |

TABLE F-1-continued

| Co. No. | Ex. No. | Structure | Physical data |
|---|---|---|---|
| 104 | B.1 | 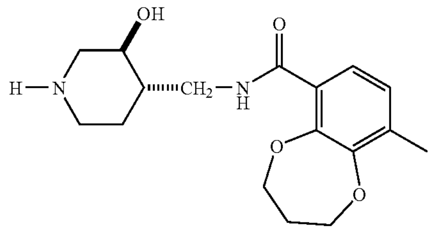 | (trans); •ethanedioate (1:1); mp. 168° C. |
| 105 | B.2 | 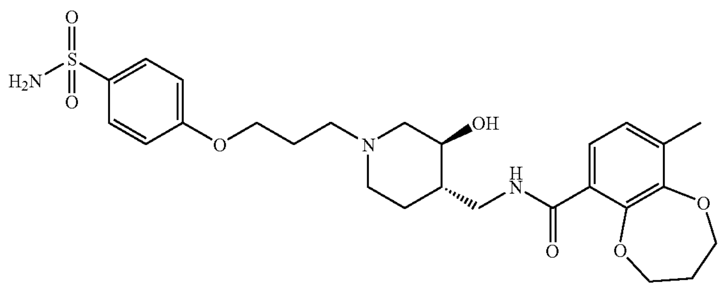 | (3S-trans); mp. 135° C.; $[\alpha]^{20,D} = -9.06°$ (c = 9.49 mg/2 ml in methanol) |
| 106 | B.2 | 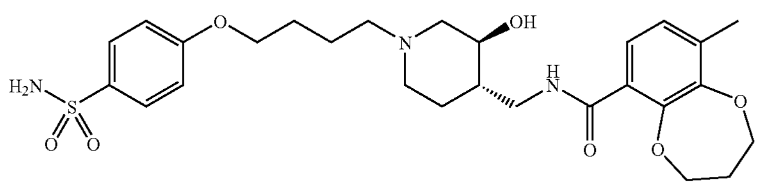 | (3S-trans); .fumarate (3:2)•2-propanol (3:2); mp. >90° C.; $[\alpha]^{20,D} = -8.93°$ (c = 21.27 mg/5 ml in methanol) |
| 107 | B.7 | 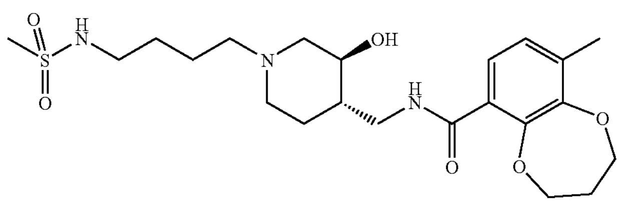 | (3S-trans); mp. 124° C. |
| 108 | B.2 | 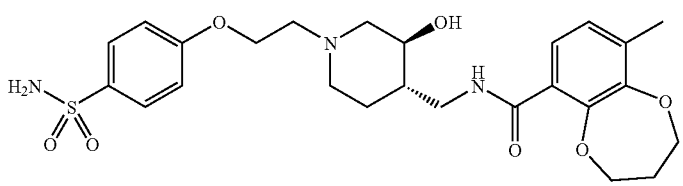 | (3S-trans); mp. 173° C. |
| 109 | B.8 | 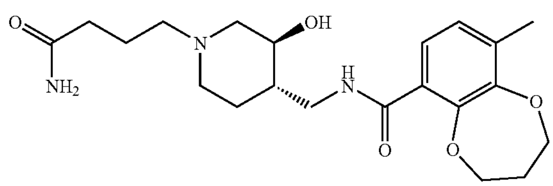 | (3S-trans); mp. 160° C.; $[\alpha]^{20,D} = -11.98°$ (c = 25.05 mg/5 ml in methanol) |
| 110 | B.2 | 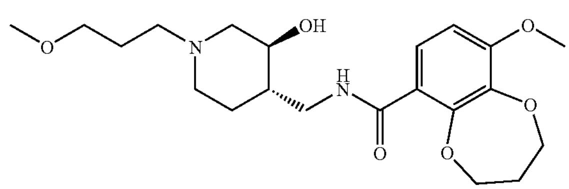 | (3S-trans); $[\alpha]^{20,D} = -9.32°$ (c = 10.30 mg/2 ml in methanol) |

TABLE F-1-continued

| Co. No. | Ex. No. | Structure | Physical data |
|---|---|---|---|
| 111 | B.2 | 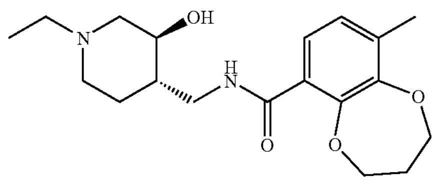 | (3S-trans); mp. 140° C.; $[\alpha]^{20,D} = -15.43°$ (c = 10.50 mg/2 ml in methanol) |
| 112 | B.2 | 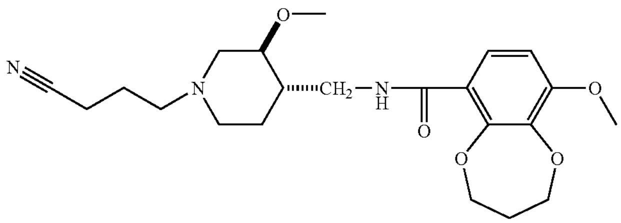 | (trans); mp. 98° C. |
| 113 | B.2 | 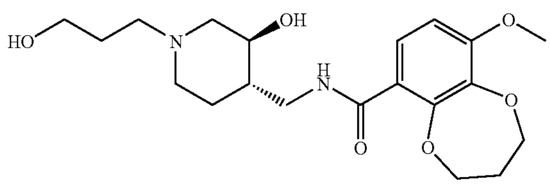 | (3S-trans); mp. 162° C.; $[\alpha]^{20,D} = -8.46°$ (c = 12.30 mg/2 ml in methanol) |
| 114 | B.5 | 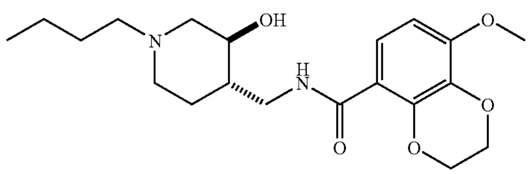 | (trans); mp. 147° C. |
| 115 | B.5 | 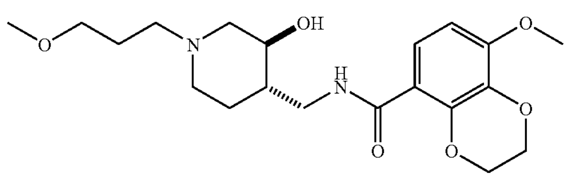 | (trans); mp. 161° C. |
| 116 | B.5 | 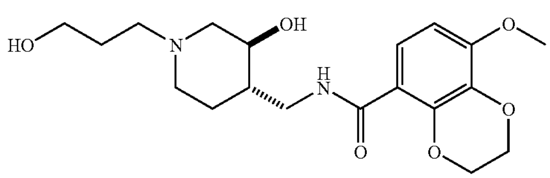 | (trans); mp. 172° C. |
| 117 | B.1 | 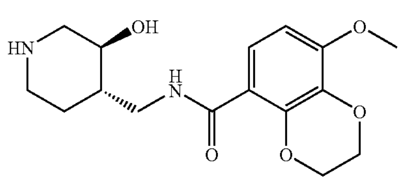 | (3S-trans); mp. 160° C. |
| 118 | B.4 | 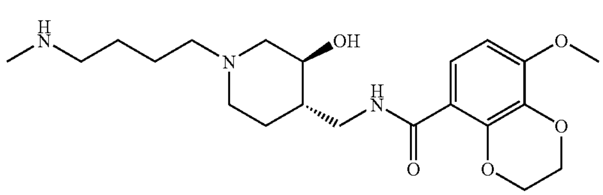 | (3S-trans); •HCl (4:9) H$_2$O (1:2); mp. 120° C. |

TABLE F-1-continued

| Co. No. | Ex. No. | Structure | Physical data |
|---|---|---|---|
| 119 | B.2 | 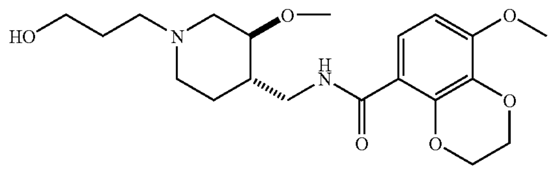 | (trans); •ethanedioate (1:1); mp. 83° C. |
| 120 | B.2 | 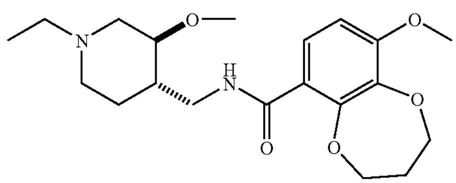 | (trans); •ethanedioate (1:1); mp. 75.2-79.8° C. |
| 121 | B.2 | 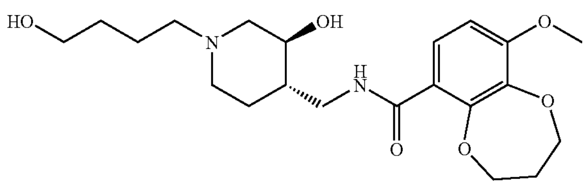 | (3S-trans); •H$_2$O (1:1); [α]$^{20,D}$ = −8.49° (c = 11.54 mg/2 ml in methanol) |
| 122 | B.2 | 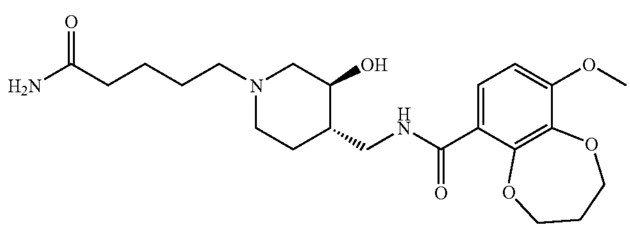 | (3S-trans); [α]$^{20,D}$ = −7.98° (c = 11.28 mg/2 ml in methanol) |
| 123 | B.6 | 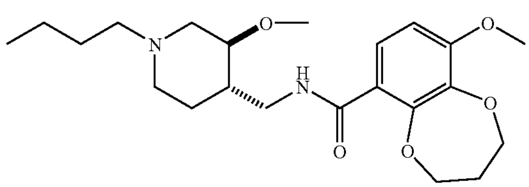 | (trans); |
| 124 | B.2 | 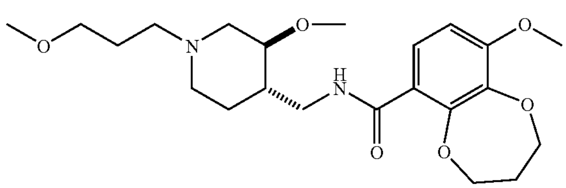 | (trans); •ethanedioate (1:1); mp. 135.7-140.6° C. |
| 125 | B.2 | 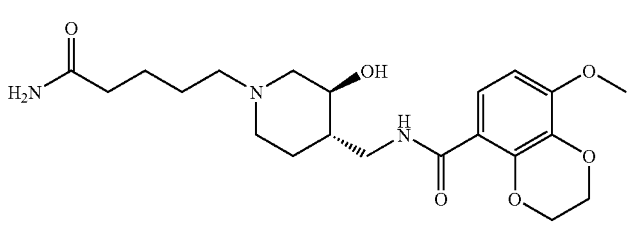 | (3S-trans); mp. 202° C; [α]$^{20,D}$ = −10.96° (c = 23.73 mg/5 ml in methanol) |

TABLE F-1-continued

| Co. No. | Ex. No. | Structure | Physical data |
|---|---|---|---|
| 126 | B.2 | 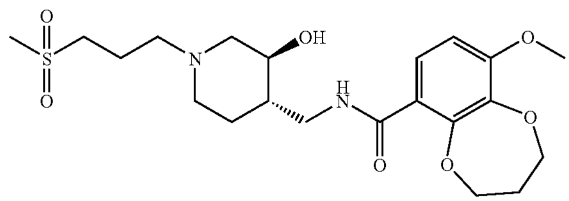 | (3S-trans); $[\alpha]^{20,D} = -6.54°$ (c = 10.70 mg/2 ml in methanol) |
| 127 | B.2 | 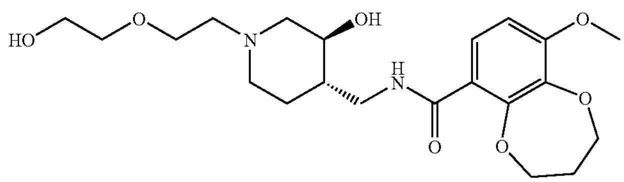 | (3S-trans); $[\alpha]^{20,D} = -7.92°$ (c = 10.60 mg/2 ml in methanol) |
| 128 | B.9 | 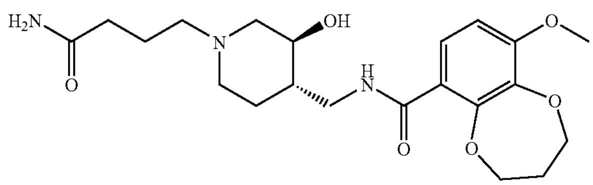 | (3S-trans); mp. 155° C. |
| 129 | B.2 | 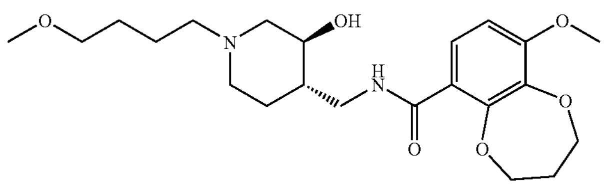 | (3S-trans); •ethanedioate (1:1); mp. 70° C. |
| 130 | B.10 | 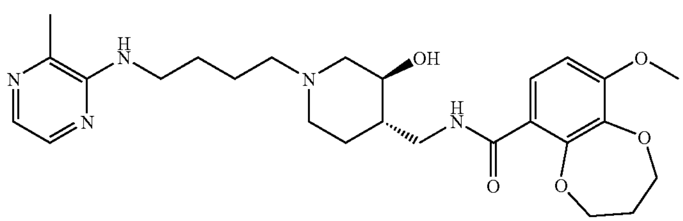 | (3S-trans); mp. 80° C. |
| 131 | B.5 | 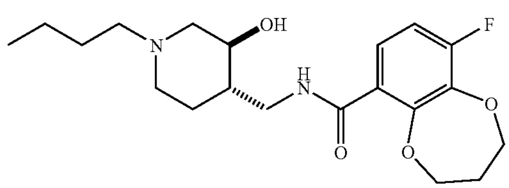 | (trans); •ethanedioate (1:1); mp. 146° C. |
| 132 | B.5 | 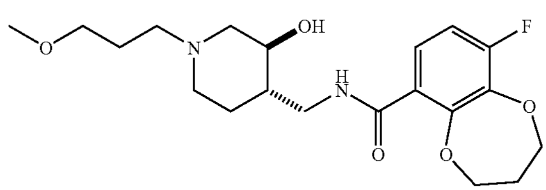 | (trans); •ethanedioate (1:1); mp. 143-145° C. |
| 133 | B.2 | 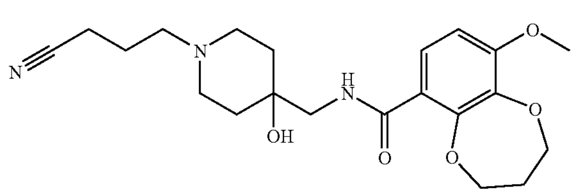 | •ethanedioate (1:1); mp. 120° C. |

TABLE F-1-continued

| Co. No. | Ex. No. | Structure | Physical data |
|---|---|---|---|
| 134 | B.2 | 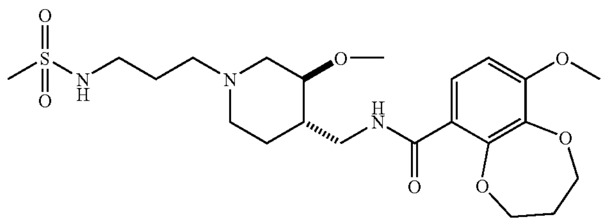 | (trans); •ethanedioate (1:1); mp. 140° C. |
| 135 | B.2 | 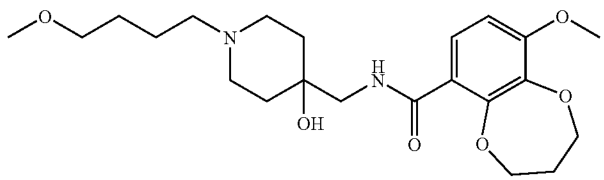 | •ethanedioate (1:1); mp. 134° C. |
| 136 | B.6 | 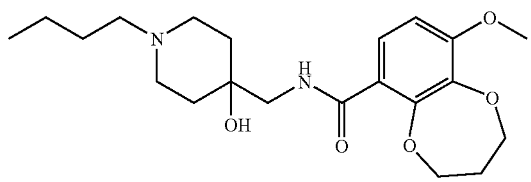 | •ethanedioate (1:1); mp. 164° C. |
| 137 | B.2 | 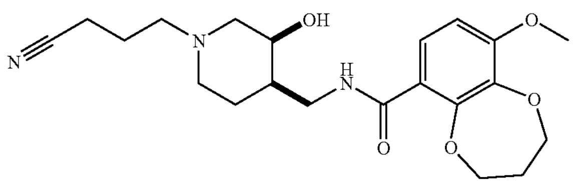 | (cis); mp. 117.4-121.2° C. |
| 138 | B.5 | 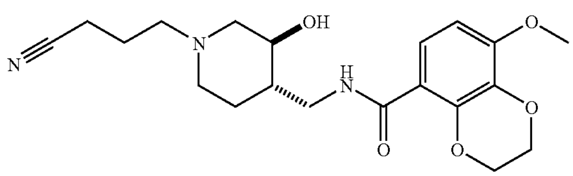 | (trans); mp. 168° C. |
| 139 | B.9 | 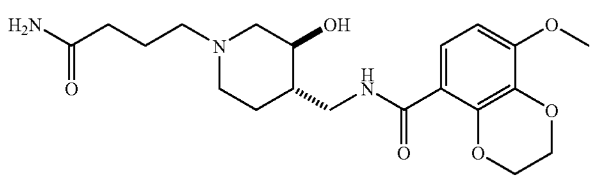 | (trans); mp. >130° C. |
| 140 | B.11 | 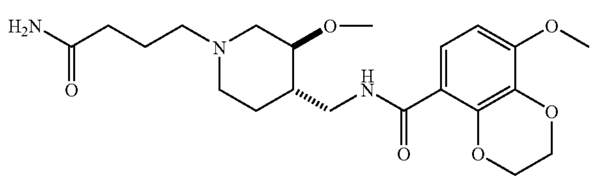 | (trans); mp. 180° C. |
| 141 | B.3 | 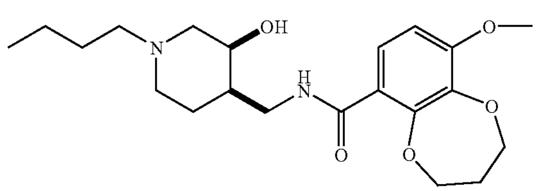 | (cis); |

TABLE F-1-continued

| Co. No. | Ex. No. | Structure | Physical data |
|---|---|---|---|
| 142 | B.2 | 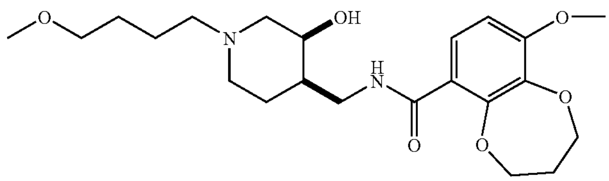 | (cis); |
| 143 | B.2 | 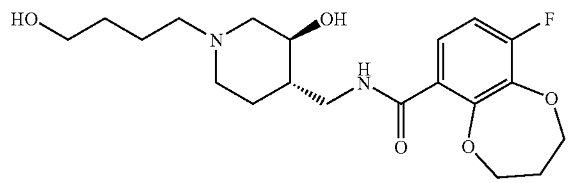 | (3S-trans); •ethanedioate (1:1); mp. >60° C. |
| 144 | B.9 | 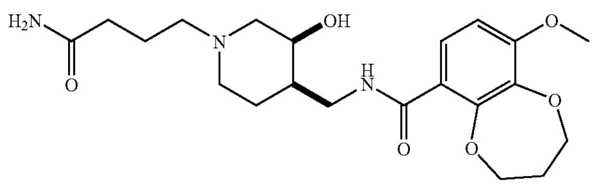 | (cis); •ethanedioate (1:1); mp. 148.1-157.5° C. |
| 145 | B.12 | 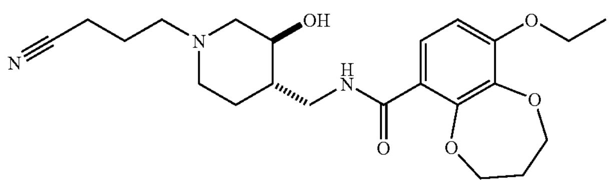 | (trans); mp. 131° C. |
| 146 | B.12 | 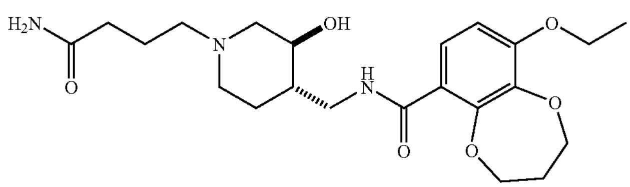 | (trans); mp. 154° C. |
| 147 | B.9 | 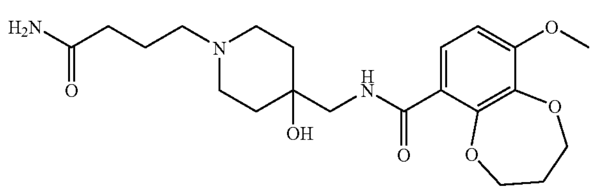 | mp. 165° C. |
| 148 | B.2 | 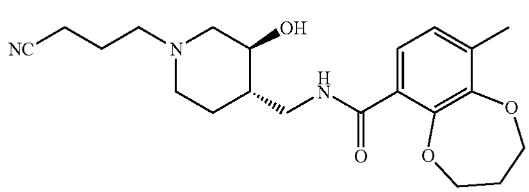 | (3S-trans); |
| 149 | B.13 | 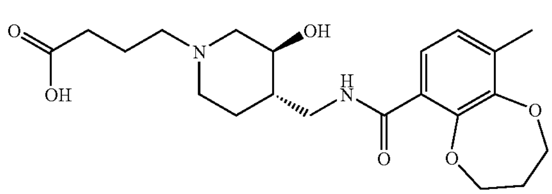 | (3S-trans); |

TABLE F-1-continued

| Co. No. | Ex. No. | Structure | Physical data |
|---|---|---|---|
| 150 | B.2 | 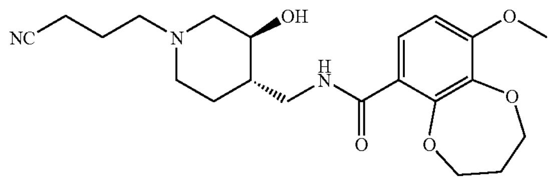 | (3S-trans); |
| 151 | B.2 | 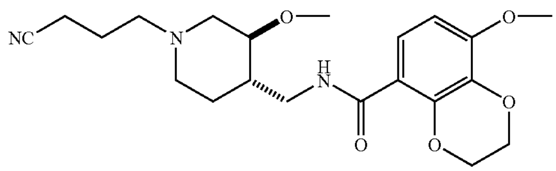 | (trans); |
| 152 | B.1 | 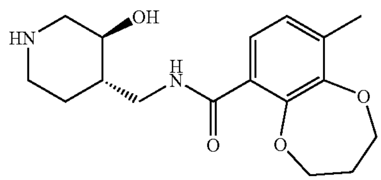 | (3S-trans); •HCl; mp. 215° C.; $[\alpha]^{20,D} = -14.03°$ (c = 23.88 mg/5 ml in methanol) |
| 153 | B.1 | 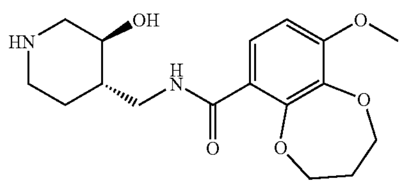 | (3S-trans); |
| 154 | B.1 | 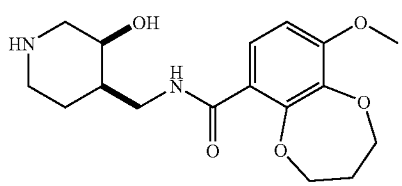 | (cis); |
| 155 | B.1 | 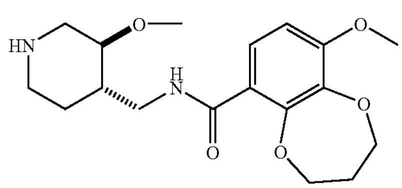 | (trans); |
| 156 | B.1 | 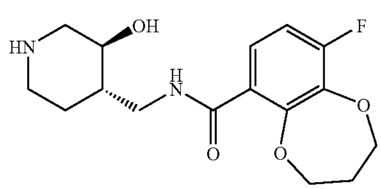 | (3S-trans); |
| 157 | B.1 | 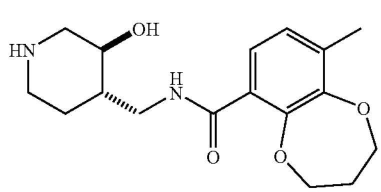 | (trans); |

TABLE F-1-continued

| Co. No. | Ex. No. | Structure | Physical data |
|---|---|---|---|
| 158 | B.5 | (structure) | (trans); |

Pharmacological Examples

Example C.1

"5HT$_4$ Antagonism"

h5-HT$_4$b-HEK 293 clone 9 cells were cultured in 150 mm Petri dishes and washed twice with cold PBS. The cells were then scraped from the plates and suspended in 50 mM Tris-HCl buffer, pH 7.4 and harvested by centrifugation at 23,500 rpm for 10 minutes. The pellet was resuspended in 5 mM Tris-HCl, pH 7.4 and homogenized with an Ultra Turrax homogenizer. The membranes were collected by centrifugation at 30,000 rpm for 20 min, resuspended in 50 mM Tris-HCl pH 7.4 and stored at −80° C. For the experiment, assay mixtures (0.5 ml) contained 50 µl of the tritiated ligand (5-HT$_4$ antagonist [$^3$H]GR113808 0.1 nM) and 0.4 ml membrane preparation (15 µg protein/ml). 50 µl of 10% DMSO was added for total binding. 50 µl of 1 µM of (+)-trans-(1-butyl-3-hydroxy4-piperidinyl)methyl 8-amino-7-chloro-2,3-dihydro-1,4-benzodioxin-5-carboxylate (a proprietary 5HT$_4$ agonist of Janssen Pharmaceutica) was added for determination of non-specific binding.

The [$^3$H]GR113808 assay buffer was 50 mM HEPES-NaOH, pH 7.4. The mixtures were incubated for 30 min at 25° C. The incubation was terminated by filtration over a Unifilter 96 GF/B presoaked in 0.1% polyethylenimine, followed by six washing steps with 50 mM HEPES-NaOH, pH 7.4.

Ligand concentration binding isotherms (rectangular hyperbola) were calculated by nonlinear regression analysis and the pIC$_{50}$ data for all tested compounds are listed below in Table C.1.

TABLE C.1

5HT$_4$ antagonistic data

| Co. No. | pIC$_{50}$ |
|---|---|
| 1 | 8.88 |
| 2 | 8.56 |
| 3 | 8.77 |
| 4 | 8.16 |
| 5 | 8.26 |
| 6 | 8.19 |
| 7 | 8.76 |
| 8 | 7.11 |
| 9 | 8.1 |
| 10 | 8.52 |
| 11 | 8.23 |
| 12 | 7.36 |
| 13 | 8.27 |
| 14 | 8.58 |
| 15 | 8.02 |
| 16 | 8.91 |
| 17 | 8.42 |

TABLE C.1-continued

5HT$_4$ antagonistic data

| Co. No. | pIC$_{50}$ |
|---|---|
| 18 | 7.62 |
| 19 | 8.57 |
| 20 | 8.44 |
| 21 | 8.41 |
| 22 | 8.85 |
| 23 | 7.76 |
| 24 | 8.75 |
| 25 | 8.51 |
| 26 | 8.2 |
| 27 | 8.31 |
| 28 | 8.2 |
| 29 | 8.19 |
| 30 | 7.9 |
| 31 | 8.15 |
| 32 | 8.06 |
| 33 | 8.92 |
| 34 | 9 |
| 35 | 7.63 |
| 36 | 7.42 |
| 37 | 8.41 |
| 38 | 8.53 |
| 39 | 8.41 |
| 40 | 7.85 |
| 41 | 7.79 |
| 42 | 7.56 |
| 43 | 7.63 |
| 44 | 7.54 |
| 45 | 8.13 |
| 46 | 8.22 |
| 48 | 7.24 |
| 49 | 8.09 |
| 50 | 8.36 |
| 51 | 8.29 |
| 52 | 6.34 |
| 53 | 7.7 |
| 54 | 8.31 |
| 55 | 6.78 |
| 56 | 8.41 |
| 57 | 7.44 |
| 58 | 8.63 |
| 59 | 8.43 |
| 60 | 7.45 |
| 61 | 7.07 |
| 62 | 6.31 |
| 63 | 8.01 |
| 64 | 8.81 |
| 65 | 8.35 |
| 66 | 6.88 |
| 67 | 7.65 |
| 68 | 7.03 |
| 69 | 7.1 |
| 70 | 6.58 |
| 71 | 7.97 |
| 72 | 7.67 |
| 73 | 7.74 |
| 74 | 8.27 |
| 75 | 8.51 |

TABLE C.1-continued

5HT$_4$ antagonistic data

| Co. No. | pIC$_{50}$ |
|---|---|
| 76 | 7.66 |
| 77 | 8.05 |
| 78 | 6.76 |
| 79 | 6.64 |
| 80 | 8.2 |
| 81 | 8.68 |
| 82 | 8.08 |
| 83 | 7.19 |
| 84 | 8.28 |
| 85 | 8.57 |
| 86 | 9.04 |
| 87 | 7.51 |
| 88 | 8.65 |
| 89 | 8.68 |
| 90 | 8.69 |
| 91 | 7.87 |
| 92 | 6.31 |
| 94 | 8.73 |
| 95 | 8.99 |
| 96 | 9.01 |
| 97 | 7.25 |
| 98 | 8.58 |
| 99 | 8.14 |
| 100 | 9.48 |
| 101 | 8.61 |
| 102 | 8.19 |
| 103 | 8.06 |
| 104 | 7.55 |
| 105 | 9.22 |
| 106 | 9.09 |
| 107 | 8.61 |
| 108 | 8.75 |
| 109 | 8.93 |
| 110 | 8.51 |
| 111 | 9.06 |
| 112 | 7.14 |
| 113 | 8.49 |
| 114 | 8.58 |
| 115 | 7.93 |
| 116 | 8.28 |
| 117 | 6.97 |
| 118 | 8.17 |
| 119 | 7.69 |
| 120 | 7.55 |
| 121 | 8.34 |
| 122 | 8.39 |
| 123 | 7.96 |
| 124 | 7.61 |
| 125 | 8.49 |
| 126 | 8.1 |
| 127 | 7.86 |
| 128 | 8.14 |
| 129 | 8.47 |
| 130 | 8.41 |
| 131 | 9 |
| 132 | 8.65 |
| 133 | 7.95 |
| 134 | 9.04 |
| 135 | 6.74 |
| 136 | 7.04 |
| 137 | 6.81 |
| 138 | 8.21 |
| 139 | 8.23 |
| 140 | 7.47 |
| 141 | 6.67 |
| 142 | 6.79 |
| 143 | 8.93 |
| 144 | 6.55 |
| 145 | 8.06 |
| 146 | 8.23 |
| 147 | 6.3 |

Example C.2

"Metabolic Stability"

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4).

Tissue homogenates were centrifuged at 9000×g for 20 minutes at 4° C. The resulting supernatant was stored at −80° C. and is designated 'S9'.

The S9 fraction can be further centrifuged at 100.000×g for 60 minutes (4° C.). The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 µM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 minutes at 95 degrees Celsius) microsomes. Recovery of the compounds in the control samples was always 100%.

The mixtures were preincubated for 5 minutes at 37 degrees Celsius. The reaction was started at time point zero (t=0) by addition of 0.8 mM NADP and the samples were incubated for 60 minutes (P60). The reaction was terminated by the addition of 2 volumes of DMSO. Then the samples were centrifuged for 10 minutes at 900×g and the supernatants were stored at room temperature for no longer as 24 hours before analysis. All incubations were performed in duplo. Analysis of the supernatants was performed with LC-MS analysis. Elution of the samples was performed on a Xterra MS C18 (50×4.6 mm, 5 µm, Waters, US). An Alliance 2790 (Supplier: Waters, US) HPLC system was used. Elution was with buffer A (25 mM ammoniumacetate (pH 5.2) in H$_2$O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 minute in a linear fashion and organic phase concentration was kept stationary for an additional 1.5 minutes. Total injection volume of the samples was 25 µl.

A Quatro triple quadrupole mass spectrometer fitted with and ESP source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 second.

Metabolic stability was expressed as % metabolism of the compound after 15 or 60 minutes (equation given as example) of incubation in the presence of active microsomes (E(act))

$$\% \text{ metabolism} = 100\% - \left(\left(\frac{\text{Total Ion Current}\,(TIC)\,\text{of}\ E(\text{act})\,\text{at}\ t = 15\ \text{or}\ 60}{TIC\ \text{of}\ E(\text{act})\,\text{at}\ t = 0}\right) \times 100\right).$$

a stereochemically isomeric form thereof, an N-oxide form thereof, or a pharmaceutically acceptable acid or base addition salt thereof, wherein —$R^1$—$R^2$— is a bivalent radical of formula $$—O—CH_2—CH_2—CH_2—O— \quad (a\text{-}5),$$

wherein in said bivalent radicals optionally one or two hydrogen atoms on the same or a different carbon atom may be replaced by $C_{1-6}$alkyl or hydroxy, $R^3$ is halo;
$R^4$ is halo;

TABLE C.2

% metabolised compound of the present invention (left column) compared analogous structures of WO-00/37461 (right column)

| Comparative structures of present invention | % | Comparative structures of WO-00/37461 | % |
|---|---|---|---|
| 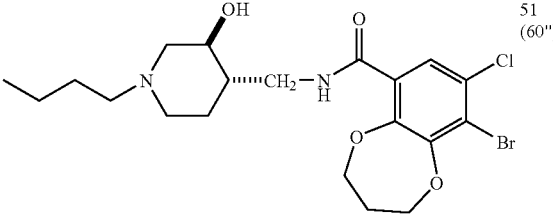<br>Co. No. 22 (trans) | 51 (60") | 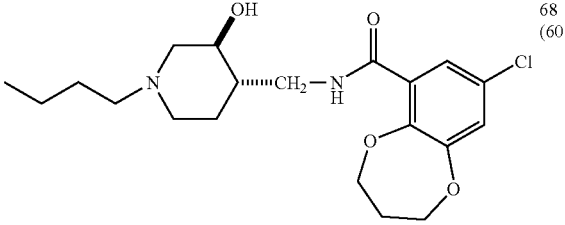<br>Co. No. 119 (trans) | 68 (60") |
| 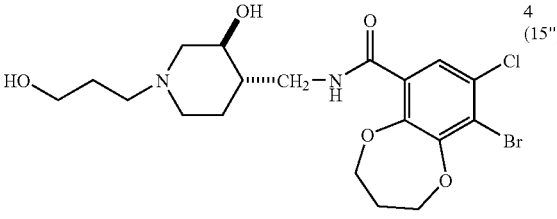<br>Co. No. 24 | 4 (15") | 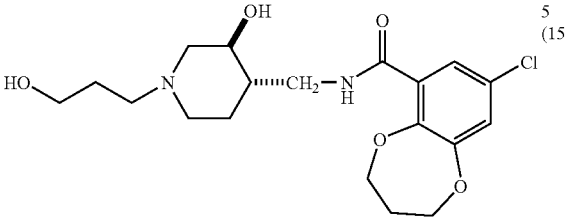<br>Co. No. 144 (trans) | 5 (15") |
| 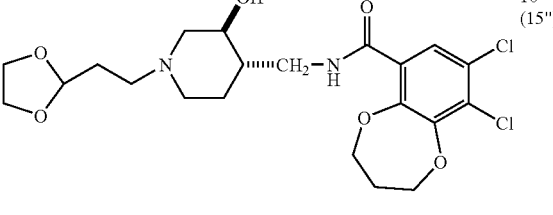<br>Co. No. 88 | 10 (15") | 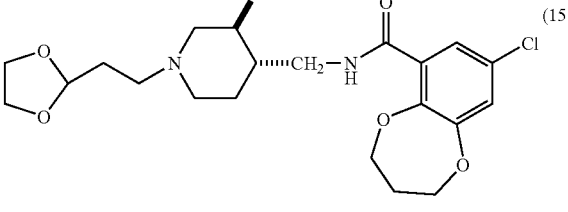<br>Co. No. 143 (trans) | 26.5 (15") |

The invention claimed is:
1. A compound of formula (I)

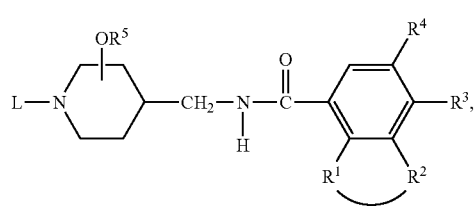

$R^5$ is hydrogen or $C_{1-6}$alkyl, and the —$OR^5$ radical is situated at the 3- or 4-position of the piperidine moiety;

L is hydrogen, or L is a radical of formula

-Alk-$R^6$ (b-1),

-Alk-X—$R^7$ (b-2),

-Alk-Y—C(=O)—$R^9$ (b-3), or

-Alk-Z-C(=O)—$NR^{11}R^{12}$ (b-4), wherein each Alk is $C_{1-12}$alkanediyl; and
$R^6$ is hydrogen; hydroxy; cyano; $C_{3-6}$cycloalkyl; $C_{1-6}$alkylsulfonylamino; aryl or Het;
$R^7$ is $C_{1-6}$alkyl; $C_{1-6}$alkyl substituted with hydroxy; $C_{3-6}$cycloalkyl; aryl or Het;

X is O, S, SO$_2$ or NR$^8$; said R$^8$ being hydrogen or C$_{1-6}$alkyl;
R$^9$ is hydrogen, C$_{1-6}$alkyl, C$_{3-6}$cycloalkyl, hydroxy or aryl;
Y is a direct bond, or NR$^{10}$ wherein R$^{10}$ is hydrogen or C$_{1-6}$alkyl;
Z is a direct bond, O, S, or NR$^{10}$ wherein R$^{10}$ is hydrogen or C$_{1-6}$alkyl;
R$^{11}$ and R$^{12}$ each independently are hydrogen, C$_{1-6}$alkyl, C$_{3-6}$cycloalkyl, or R$^{11}$ and R$^{12}$ combined with the nitrogen atom bearing R$^{11}$ and R$^{12}$ may form a pyrrolidinyl, piperidinyl, piperazinyl or 4-morpholinyl ring both being optionally substituted with C$_{1-6}$alkyl;
aryl represents unsubstituted phenyl or phenyl substituted with 1, 2 or 3 substituents each independently selected from halo, hydroxy, C$_{1-6}$alkyl, C$_{1-6}$alkyloxy, C$_{1-6}$alkylcarbonyl, nitro, trifluoromethyl, amino, aminocarbonyl, and aminosulfonyl; and
Het is furanyl; furanyl substituted with C$_{1-6}$alkyl or halo; tetrahydrofuranyl; tetrahydrofuranyl substituted with C$_{1-6}$alkyl;
dioxolanyl; dioxolanyl substituted with C$_{1-6}$alkyl;
dioxanyl; dioxanyl substituted with C$_{1-6}$alkyl;
tetrahydropyranyl; tetrahydropyranyl substituted with C$_{1-6}$alkyl;
2,3-dihydro-2-oxo-1H-imidazolyl; 2,3-dihydro-2-oxo-1H-imidazolyl substituted with one or two substituents each independently selected from halo, or C$_{1-6}$alkyl;
pyrrolidinyl; pyrrolidinyl substituted with one or two substituents each independently selected from halo, hydroxy, or C$_{1-6}$alkyl;
pyridinyl; pyridinyl substituted with one or two substituents each independently selected from halo, hydroxy, C$_{1-6}$alkyl;
pyrimidinyl; pyrimidinyl substituted with one or two substituents each independently selected from halo, hydroxy, or C$_{1-6}$alkyl;
pyridazinyl; pyridazinyl substituted with one or two substituents each independently selected from hydroxy, C$_{1-6}$alkyloxy, C$_{1-6}$alkyl or halo;
pyrazinyl; pyrazinyl substituted with one ore two substituents each independently selected from hydroxy, C$_{1-6}$alkyloxy, C$_{1-6}$alkyl or halo.

2. The compound as claimed in claim 1 wherein the —OR$^5$ radical is situated at the 3-position of the piperidine moiety having the trans configuration.

3. The compound as claimed in claim 2 wherein the absolute configuration of said piperidine moiety is (3S, 4S).

4. The compound as claimed in claims 1 wherein —R$^1$—R$^2$— is a radical of formula (a-5), R$^3$ is chloro and R$^4$ is chloro.

5. The compound as claimed in claim 1 wherein —R$^1$—R$^2$— is a radical of formula (a-5), R$^3$ is chloro and R$^4$ is bromo.

6. A pharmaceutical composition comprising a pharmaceutically acceptable carrier and a therapeutically active amount of a compound according to claim 1.

7. A method for treating hypermotility, irritable bowel syndrome, constipation or diarrhea predominant IBS, pain and non-pain predominant IBS and bowel hypersensitivity comprising administering to a patient in need thereof an effective amount of a compound according to claim 1.

8. A process for preparing a compound of formula (I) wherein
a) an intermediate of formula (II) is reacted with an carboxylic acid derivative of formula (III) or a reactive functional derivative thereof;

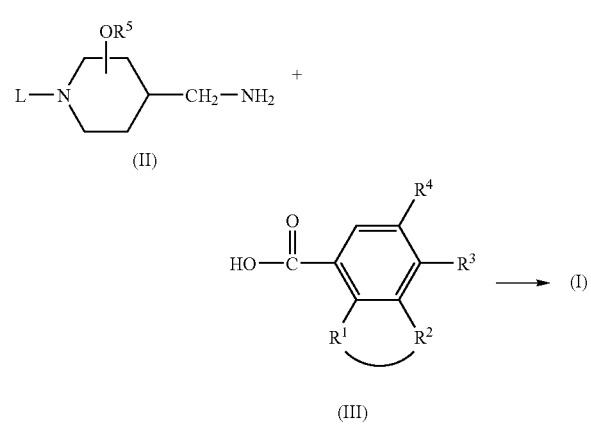

b) an intermediate of formula (IV) is N-alkylated with a compound of formula (I-a), defined as a compound of formula (I) wherein L represents hydrogen, in a reaction-inert solvent and, optionally in the presence of a suitable base, thereby yielding compounds of formula (I-b), defined as compounds of formula (I) wherein L is other than hydrogen;

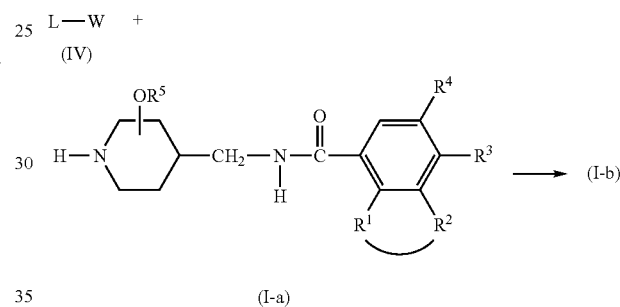

c) an appropriate ketone or aldehyde intermediate of formula L'=O (V), said L'=O being a compound of formula L-H, wherein two geminal hydrogen atoms in the C$_{1-12}$alkanediyl moiety are replaced by =O, is reacted with a compound of formula (I-a), thereby yielding compounds of formula (I-b);

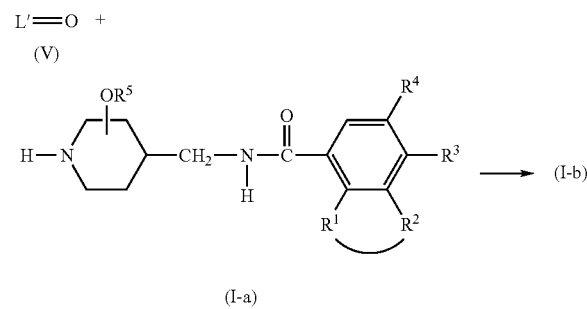

wherein in the above reaction schemes the radicals —R$^1$—R$^2$—R$^3$, R$^4$ and R$^5$ are as defined in claim 1 and W is an appropriate leaving group;
d) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

* * * * *

UNITED STATES PATENT AND TRADEMARK OFFICE
CERTIFICATE OF CORRECTION

PATENT NO.        : 7,635,706 B2                                         Page 1 of 1
APPLICATION NO.   : 10/560485
DATED             : December 22, 2009
INVENTOR(S)       : Jean-Paul René Marie André Bosmans et al.

It is certified that error appears in the above-identified patent and that said Letters Patent is hereby corrected as shown below:

Title Page,
Item (22) PCT Filed:
Delete "Aug. 10, 2004" and insert -- Jun. 10, 2004 --.

Column 2,
Line 32, delete "$C_{1-6}$allyl,," and insert -- $C_{1-6}$alkyl, --.

Column 8,
Line 10, delete "(VII)." and insert -- (VIII). --.

Column 12,
Line 2, delete ""$NE_4OAc$"" and insert -- "$NH_4OAc$" --.

Column 94,
Lines 55-56, delete "–$R^1$–$R^2$–$R^3$," and insert -- –$R^1$–$R^2$–, $R^3$, --.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,635,706 B2 Page 1 of 1
APPLICATION NO. : 10/560485
DATED : December 22, 2009
INVENTOR(S) : Bosmans et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this

Ninth Day of November, 2010

David J. Kappos
*Director of the United States Patent and Trademark Office*